(12) United States Patent
Rothschild et al.

(10) Patent No.: US 6,678,703 B2
(45) Date of Patent: Jan. 13, 2004

(54) MEDICAL IMAGE MANAGEMENT SYSTEM AND METHOD

(75) Inventors: Peter Alden Rothschild, Redwood City, CA (US); Vijendra Guru Raaj Prasad, Fremont, CA (US)

(73) Assignee: Radvault, Inc., Hayward, CA (US)

( * ) Notice: Subject to any disclaimer, the term of this patent is extended or adjusted under 35 U.S.C. 154(b) by 322 days.

(21) Appl. No.: 09/771,446

(22) Filed: Jan. 25, 2001

(65) Prior Publication Data

US 2002/0019751 A1 Feb. 14, 2002

Related U.S. Application Data

(63) Continuation-in-part of application No. 09/602,643, filed on Jun. 22, 2000.

(51) Int. Cl.$^7$ ................................................ G06F 17/30
(52) U.S. Cl. ............................... 707/201; 707/2; 707/3; 707/10; 707/104; 382/132; 705/3
(58) Field of Search .......................... 707/3, 2, 10, 101, 707/102, 104, 201; 709/229; 705/2, 37, 3; 382/128, 132

(56) References Cited

U.S. PATENT DOCUMENTS

| | | | |
|---|---|---|---|
| 4,847,694 A | 7/1989 | Nishihara | |
| 4,958,283 A | 9/1990 | Tawara et al. | |
| 4,993,025 A | 2/1991 | Vesel et al. | |
| 5,124,789 A | 6/1992 | Hiyama et al. | |
| 5,140,518 A | 8/1992 | Ena | |
| 5,231,572 A | 7/1993 | Shigyo et al. | |
| 5,235,510 A | 8/1993 | Yamada et al. | |
| 5,321,520 A | 6/1994 | Inga et al. | |
| 5,374,965 A | 12/1994 | Kanno | |
| 5,384,643 A | 1/1995 | Inga et al. | |
| 5,416,602 A | 5/1995 | Inga et al. | |
| 5,469,353 A | 11/1995 | Pinsky et al. | |
| 5,502,576 A | 3/1996 | Ramsay et al. | |
| 5,502,726 A | 3/1996 | Fischer | |
| 5,513,101 A | 4/1996 | Pinsky et al. | |
| 5,586,262 A | 12/1996 | Komatsu et al. | |
| 5,654,555 A | 8/1997 | Butaert et al. | |
| 5,655,084 A | 8/1997 | Pinksy et al. | |

(List continued on next page.)

FOREIGN PATENT DOCUMENTS

| WO | WO 99 18502 A | 4/1999 |
|---|---|---|
| WO | WO 00 33157 A | 6/2000 |
| WO | WO 00 33231 A | 6/2000 |

OTHER PUBLICATIONS

Patent Abstracts of Japan vol. 2000, No. 01, Jan. 31, 2000 & JP 11 284974 A (Fuji Photo Film Co. Ltd.), Oct. 15, 1999 abstract.

Patent Abstracts of Japan vol. 2000, No. 01, Jan. 31, 2000 & JP 11 284682 A (Fuji Photo Film Co. Ltd.), Oct. 15, 1999 abstract.

*Primary Examiner*—Jean M. Corrielus
(74) *Attorney, Agent, or Firm*—Susan M. Schmitt

(57) ABSTRACT

The present invention provides a medical image management system and method that uses a central data management system to centrally manage the storage and transmission of electronic records containing medical images between remotely located facilities. A polling system is provided with remotely located workstations or local workstations so that the remote or local workstations may request queued data to be delivered that is awaiting delivery in the central database management system. The remotely located workstation or local image workstation communicates with a remotely located central data management system via a remote interface over the internet. The central database management system maintains and update any changes in the IP address of a remote or local workstation, in a look up table. The central data management system may also, in addition, push data when received to the last known IP address in the look up table.

34 Claims, 13 Drawing Sheets

U.S. PATENT DOCUMENTS

| | | |
|---|---|---|
| 5,668,998 A | 9/1997 | Mason et al. |
| 5,671,353 A | 9/1997 | Tian et al. |
| 5,715,823 A | 2/1998 | Wood et al. |
| 5,734,915 A | 3/1998 | Roewer |
| 5,740,428 A | 4/1998 | Mortimore et al. |
| 5,793,969 A | 8/1998 | Kamentsky |
| 5,851,186 A | 12/1998 | Wood et al. |
| 5,857,030 A | 1/1999 | Goborski et al. |
| 5,897,498 A | 4/1999 | Canfield, II et al. |
| 5,949,491 A | 9/1999 | Callahan et al. |
| 5,950,207 A | 9/1999 | Mortmore et al. |
| 5,959,678 A | 9/1999 | Callahan et al. |
| 6,006,191 A * | 12/1999 | DiRienzo ...................... 705/2 |
| 6,047,081 A | 4/2000 | Groezinger et al. |
| 6,101,407 A | 8/2000 | Groezinger |
| 6,115,486 A | 9/2000 | Cantoni |
| 6,117,079 A | 9/2000 | Brackett et al. |
| 6,128,655 A * | 10/2000 | Fields et al. ................. 709/219 |
| 6,137,527 A | 10/2000 | Abdel-Malek et al. |
| 6,159,150 A | 12/2000 | Yale et al. |
| 6,171,244 B1 | 1/2001 | Finger et al. |
| 6,178,225 B1 | 1/2001 | Zur et al. |
| 6,192,407 B1 * | 2/2001 | Smith et al. ................. 709/229 |
| 6,210,327 B1 | 4/2001 | Brackett et al. |
| 6,487,599 B1 * | 11/2002 | Smith et al. ................. 709/229 |
| 2001/0032263 A1 * | 10/2001 | Gopal et al. ................. 709/227 |

* cited by examiner

MEDICAL IMAGE MANAGEMENT SYSTEM AND METHOD

This application is a continuation-in-part of 09/602,643 filed Jun. 22, 2000.

TECHNICAL FIELD

The present invention is a system and method for managing medical images. More specifically, it is a computer-based system and method for capturing, transmitting, storing, processing, and communicating electronic records associated with medical images.

BACKGROUND

Diagnostic imaging technology has evolved tremendously in the past twenty years, offering very sophisticated imaging tests such as magnetic resonance imaging (MRI) and computed tomography (CT). The MRI market in particular includes approximately 6,000 MRI machines in the United States, and 12,000 worldwide. Two-thirds of MRI devices in the US are located clinics and small hospitals. There are over 12,000 CT scanners in the United States and over 20,000 worldwide. Other significant medical imaging markets include for example, ultrasound, nuclear medicine, digital x-ray, and computerized radiology. On the aggregate, the potential medical image management market has been estimated at $5.5 Billion annually in the US and $12 Billion worldwide.

The need for immediate electronic delivery and convenient, economic storage of radiologic and other medical images and data has never been greater. The annual United States radiology market consists of more than 150 million x-rays, 100 million sonograms, 20 million MRI scans and 30 million CT scans performed by medical practitioners. The conventional process for managing medical images at most hospitals, clinics and imaging centers is as follows. The medical image is printed onto sheets of film, which are delivered to the radiologist for interpretation. After the transcribed report is delivered to the radiologist, reviewed for errors and signed, the films and report are delivered or mailed to the referring doctor. This process often takes several days, up to a week. If questions arise, the referring doctor contacts the radiologist, who may be forced to rely upon memory, having reviewed the films several days before and no longer has possession of them. Also, the referring doctor must then manage the hard-copy films, either by filing the films in his office, or returning the films to the imaging center or hospital to be filed, depending upon practices in the local community. If the patient then goes to a second doctor, requires surgery, or requires another medical imaging procedure, the films must be located and physically carried or shipped to the hospital, surgery center, or to the second doctor's office. There are numerous opportunities for films to be lost or misfiled, and doctors who maintain more than, one office may not always have the correct patient films in the correct office.

The current film-based system is very expensive, and the charges for films, processing chemicals, and delivery can easily add up to $30 to $50 per MRI patient study. A typical MRI center scanning 300 patients per month has equivalent costs of approximately $12,000 per month ($40 per study× 300 patients/month). Other problems for the imaging facility are the numerous opportunities for the films to be physically lost, as well as the considerable time, personnel, and expense required for the delivery and retrieval of these films. Estimates are that up to 25% of medical images are not accessible when required.

Currently, no widely established commercial Internet solution exists for the digital delivery and archiving of the ever-increasing vast stores of radiologic data. Many patients are accustomed to sending email with various attachments, such as files or photos, and wonder why radiology images cannot be "emailed" to their doctors. However, several barriers exist for a medical image to be "emailed" to the doctor.

In order to electronically transport medical images efficiently, the images must be in a digital format. The imaging device, such as the MRI machine, must have the computer interfacing hardware and software configured to "export" the data. A computer is needed to convert the proprietary image identification data (the header information) into a standardized format, such as DICOM (Digital Imagine, and Communication in Medicine). Also, the doctor who receives the images must have software that allows him or her to view the medical images and interpret the image header information (viewer). However, non-DICOM enabled models represent the majority of imaging machines. Due to financial constraints imposed by managed care on imaging centers, non-DICOM machines will continue to dominate diagnostic imaging for the foreseeable future.

When digital modalities such as CT and MRI first came into general clinical use, each manufacturer used its own proprietary means of reconstructing the data, formatting files and storing each of the studies. They did not share this basic information with other competing manufacturers; therefore, one set of images could not be communicated to another machine since each had a different format. In 1983, the American College of Radiology and the National Electronic Manufacturers Association met to discuss a standard. In early 1984 the two organizations formed the Digital Imaging and Communication in Medicine (DICOM) Standards Committee. After many years of extensive work, the first DICOM model was introduced in 1992. By late 1994, a few manufacturers had begun to offer to incorporate DICOM into their products, usually as an expensive ($20,000–$40,000) upgrade. However, even today, the majority of these manufacturers still today only incorporate DICOM in their new products for a significant extra charge ($20,000-$40,000). Many of the older established medical imaging systems do not even have a DICOM conversion available from the original equipment manufacturer. Whenever a DICOM conversion upgrade is available for already built and installed products, it is usually even more expensive than DICOM for a new product. DICOM is a communications standard and does not define particular hardware architecture. It permits integration of images into non-image databases and is the predominant standard for medical image communication. It enjoys broad support across specialties and other standards organizations throughout the world.

Interfaces have been developed to "DICOM enable" imaging systems that were not originally factory equipped with DICOM. Without supplying DICOM interfaces as a component of an overall system, a medical image management system in the general field contemplated by the invention would be required to take one of three courses of action: 1) limit their imaging center users to DICOM conformant equipment, 2) purchase or require their customer to purchase and install DICOM interfaces at a cost of upwards of $40,000, or 3) rely on a technique known as secondary capture. In the case of secondary capture methods, like video frame grabbing, some of the information is lost, because it only captures the 8-bit analog representation of the original 16-bit image pixel data. Also, secondary captured images cannot be later manipulated to the same degree as the original images. Because of the inherent drawbacks of secondary captured data, the American College of Radiology (ACR) standard states that the direct capture method is preferred for primary diagnosis.

It is not believed that the general imaging center and referring physician marketplace will tolerate the use of the inferior secondary capture method, or an ASP that can only connect to DICOM equipped imaging systems. The system and method of the present invention provides DICOM connectivity. Also, in order to transmit and store images without compromising the quality or integrity of the imaging data, an efficient medical image management system is preferably able to successfully connect disparate imaging equipment and systems without compromising the image quality. To accomplish this the system should be able to extract the proprietary data from various different imaging machines, again the vast majority of which are not DICOM enabled and therefore cannot "output" the data in the DICOM format. Moreover, though DICOM is the universal industry standard, like the English language different "dialects" of DICOM exist depending on how each of the many individual manufacturers "speak" the DICOM language. What this means is that it is quite common for two systems that have DICOM interfaces to still have difficulty connecting and communicating with each other. Therefore, customization of interfacing, between such machines may be required in some circumstances.

Once these above barriers are overcome, it becomes possible to electronically transmit medical images in an efficient and readily adoptable manner. These electronic images, unlike film, can be simultaneously presented in multiple locations immediately after an imaging study is performed.

Picture Archiving and Communication Systems (PACS)

Various solutions have been developed with the intention of streamlining the storage and accessibility of medical images by managing, electronic records that include the images in electronic form that may be converted for viewing, such as on screen displays or via film printers.

One well-known type of such a system called "Picture Archiving and Communications Systems" (PACS) generally provides medical image management via a collection of components that enable image data acquisition, transmission, display, and, storage. Such systems are implemented in imaging clinics and hospitals to make the digital data available at different locations within the radiology department or the facility. Further, the use of such systems is generally restricted to in-house radiology and other departments, thus excluding the referring physicians, who are outside the imaging facility. These systems have high price tags ($60,000 to $ 1,000,000) for the local installation of the respective central image management and storage systems generally required, and involve other high costs related to additional personnel to configure and maintain such image management systems locally onsite at the imaging facility.

Medical Images and Internet ASP's

Because the medical image management market is so large, and represents such large volumes of recurring transmissions of electronic records associated with medical images, an ASP model for managing electronic images provides great potential for a highly profitable annuity business. Various efforts have recently been made to replace or at least significantly enhance the conventional film-based systems and methods for medical image management by managing these images electronically, and more particularly via an internet-based ASP model. However, the concept of an Internet based Application Service Provider (ASP) for the transmission and storage of medical images is an industry in its an embryonic stage. Very few, if any, of the over 300 diagnostic imaging procedures performed annually in the U.S. are being transmitted and/or stored utilizing an ASP model.

To transmit an image electronically as is intended with these known medical image management systems, the first step is to get the data from the imaging modality (CT, MR, ultrasound, etc.) to the image acquisition system at the customer site. There are two methods of obtaining this data: primary and secondary data capture. Because primary capture is not always possible in order to support other known medical image management systems and methods, they often use "secondary" or "indirect" methods. The simplest and oldest "secondary" capture method is often called "frame grabbing". This method simply obtains the image present on the video monitor and records it. The resulting image is only 8 bits deep allowing 256 shades of gray, which means a significant amount of image data has been lost. The use of "frame grabbing" is also very labor intensive. When using "frame grabbing", the technologists must pre-set the "window" and "level" (brightness and contrast) of the image. This requires an excessive amount of the technologist's time when compared to the more modern primary capture. These frame grabber systems work by taking the analog monitor output from a digital modality and running it through an analog-to-digital converter, which in itself degrades the data. The ability to adjust the brightness and contrast (window and level) of the image on the receiving end is also limited with images that were obtained using "secondary" capture. Measurements and position location of the image, both extremely important to the physician, are not generally possible with acceptable accuracy using secondary capture. Furthermore, due to problems described above, the latest version of the American College of Radiology (ACR) standards for teleradiology effective Jan. 1, 1999, recommends compliance to DICOM and transfer of the full image data set, which is only possible with "primary" or "direct capture" for primary diagnosis.

In general, most of the known systems and methods for managing medical images in electronic record format use "pull" type image delivery protocol which requires the referring physician to log on to a web server and then download his or her patient's images. However, busy physicians do not have the time or the desire to access their patient's images in this manner. The "pull" model requires the physician to log in as well as extensive physician input and time to initiate the data transfer. Additionally, the doctor must then wait for the image data to download.

Various more specific examples of such medical image ASP efforts are summarized in relation to respectively known companies in the general field as follows (much of the information provided immediately below is based upon information and belief, and in some cases is based only on rumor and verbal discussion—therefore the general and detailed elements for these companies may not be wholly accurate).

The following is a description of what is believed to be information related to a medical image management system to be provided by a company called "Amicas". Amicas is a private company located in Newton, Mass. that is believed to market and sell software that allows radiology studies to be sent between Web servers. The target market for Amicas is believed to be large hospitals. It is believed that Amicas plans to enable the transfer of such images between any medical facilities that have standard e-mail systems, using UPS Document Exchange (SM)—an encryption-based secure delivery service featuring optional password protection, real-time racking and delivery confirmation. The physician still must login to get his or her email, and wait for the images to download. The company is currently using the service at 4 beta sites. The Company gained FDA approval in 1997. To qualify as a potential customer a client's machines must have DICOM installed. CEO Dr. Adrian Gropper stated in an interview conducted May 2, 2000 at the E-Healthcare Conference in Las Vegas Nev. that Amicas has no plans to develop custom DICOM interfaces. Dr. Gropper has also stated that his company has no plans to offer any form of off site storage. It is further believed that the company uses lossy compression of the electronic records associated with medical images they manage. It is believed that Amicas has a test site which is located at the Loma Linda Veterans Administration Hospital.

The following is a description of what is believed to be information related to a medical image management system to be provided by a company called "eMed". eMed is a private company located in Lexington, Mass. The target users are hospitals. The eMed.net service is believed to include a medical image viewing application with integrated access to medical images and reports along with other relevant information through a physician's web site. eMed Technologies is a Healthcare Application Service Provider (HASP) and takes care of everything from server hardware, domain name registration, site creation and current content, all for a monthly subscription fee of $2,500. The company has FDA approval. The company prefers DICOM equipped machines, but is able to capture images from non-DICOM imaging machines in two ways: (1) DICOM converting device at a customer cost of up to $40,000; and (2) frame grabbing—a form of secondary capture which is believed to be unacceptable for primary diagnostic interpretation.

The following is a description of what is believed to be information related to a medical image management system to be provided by General Electric Medical Systems, Dallas, Tex. and Waukesha, Wis. stated in a press release dated Apr. 9, 2000 that GE will use an ASP model to primarily store data generated at an off-site location. It is believed that this recent announcement addresses an ASP model for GE's traditional PACS system. The press release claims that GE will pilot the program during the summer of 2000. The press release does not mention numerous details (such as connectivity to their system i.e. whether non-DICOM compliant machines will ever be offered the service; whether only GE or non-GE equipment will be targeted; whether GE plans to develop any DICOM interfaces to non-DICOM equipment; what data specifically is planned to be stored). The press release mentions a network subscription fee arrangement but does not give any pricing details. Most importantly, GE does not deliver the images, but instead has the doctors log on.

The following is a description of what is believed to be information related to a medical image management system to be provided by Image Medical, a private company located in Palo Alto, Calif. The target market is large institutions. Image Medical uses an ASP model to transmit medical images over the Internet. The Image Medical system is called "Practice Builder". It is DICOM compliant and works with existing PACS and provides the ability to access images and reports anywhere. "Practice Builder" includes a "Viewer" for digital medical images, CT, MR, US, DR, CR and NM. The revenue model is an activation fee that covers connectivity, infrastructure and installation costs. A per transaction fee is then charged for image acquisitions, distributions and archival. The company is not developing interfaces for imaging machines that are not DICOM equipped.

The following is a description of what is believed to be information related to a medical image management system to be provided by a company called "Inphact", a private company located in Nashville Tenn. Inphact claims to integrate an Internet based ASP PACS with a RIS. The target market is any hospital or clinic that is unable to afford an in-house PACS. RadWeb™ allows physicians to query radiology images 24/7 via the Internet. The company plans to extend its technology platform in the future to cardiology. The company is not believed to offer push technology, image history record system, or custom DICOM interfaces.

The following is a description of what is believed to be information related to a medical image management system to be provided by In Site One, Inc. which is located in Wallingford, Conn. The primary target market is hospitals. In Site One is a service provider offering digital image storage and archiving for the medical community. For this company, the imaging device must be DICOM compliant. "In Dex" (Internet DICOM Express) is a transaction, pay as you go service for storage and archiving of DICOM images for hospitals. In Dex's open architecture integrates with any PACS component as well as hospital networks and information systems. Images can be accessed via the Internet or through virtual private networks to a hospital's network. In Dex is suited for facilities with or without PACS capabilities. For PACS owners, In Dex enables them to outsource the storage and archiving component. For non-PACS equipped facilities, In Dex delivers storage and archival of a PACS without the high capital outlay, maintenance costs, technical upgrades and staffing support. There is no delivery of images to referring physicians nor do referring physicians have access to view the images they order.

The following is a description of what is believed to be information related to a medical image management system to be provided by Radiology.com, which is located in Los Angeles, Calif. and Chantilly, Va. The target market is hospitals. Radiology.com announced the launch of a service that allows digitized medical images to be stored and retrieved on-line through a central, web-based repository on Mar. 9, 2000. The technology combines DICOM and JAVA that allows a high level of compression and encryption of medical images for transmission to a PC. The system employs an ASP model. The company claims open standards will allow lifetime access to a global central repository of medical images, named "Image Bank". Patients can build their own imaging history through "Patient's Bank" which can be used to obtain discrete second opinions. The revenue model is a pay-as-needed approach. It is believed that this system only exists on paper and no clinical sites have been developed.

The following is a description of what is believed to be information related to a medical image management system to be provided by "Real Time Image", a private company located in San Mateo, Calif. The target market is large hospitals with PACS. PACS on Demand is a product that allows physicians to view images anywhere, anytime, even over dial-up connections. iPACS is a Web server that integrates to PACS, allowing physicians to view images directly from a DICOM archive over the Internet using Microsoft's Internet Explorer™ or Netscape Navigator™ Web-browsers. The user must install plug-in to his or her browser before attempting any use of this product. iPACS "streams" images on the fly using original image data without pre-processing or requiring separate archives.

The following is a description of what is believed to be information related to a medical image management system to be provided by "Stentor", a company located in the Silicon Valley. The target market is hospitals with existing Intranets. The Stentor system is PC based. Stentor's "iSYN-TAX" technology delivers images only over existing hospital networks. Stentor has FDA approval. Stentor claims its iSYNTAX system will integrate into any existing hospital network. Stentor can send real time images on as slow as a 1 megabyte per second network connection. Images are encoded using a wavelet technology. A lossless representation of the transmitted image is claimed; however, lossless transmission (as the present invention performs) is not claimed. Stentor claims no bills will be sent until real savings by the imaging department have been demonstrated. Stentor charges on a per use basis.

None of the other known electronic image management sytems and methods intended to provide an ASP model adequately address the needs of referring physicians and other parties in the healthcare provider stream outside of the imaging clinic.

In one regard, other systems intending to provide a medical image ASP service generally require timely log-on and download procedures at the physician terminal. In another regard, none of the other systems and methods intended to provide a medical image ASP are believed to provide the image center with a history record of where and when images are sent, received, and viewed. However, a system which pushes the images directly to remotely located desktops of interested healthcare providers or patients outside of the imaging clinic would be much more resource efficient at their end. Furthermore, medical imaging centers producing the electronic images would benefit from a system which provides them with a real-time, image history record with easily accessible information about the times and places that each image is sent, received, and viewed at all locations.

Also, other efforts intended to provide a cost-effective ASP generally require costly hardware investment, principally on the part of the respective imaging center, and according to some of these efforts per-use fees are charged for each image viewing occasion. However, smaller imaging clinics and healthcare providers outside of the imaging center would benefit from a business model which provides the associated image work-stations necessary to use the ASP without requiring capital expenditure on the hardware or software. These parties would be greatly benefited by a method that provides a medical image ASP on a monthly service fee only basis, without up-front hardware costs, and without costly "per-use" transaction fees. Moreover, by providing a medical image ASP that charges only the imaging clinics on a fixed fee basis, these centers would be able to solely enjoy the economic benefits of their increased revenues flowing from increased image volume, at least to the extent that such volume is charged through to payers. In particular, the imaging center would benefit from an electronic medical image ASP system that charges only fixed or per use fees, but that provides without direct capital expenditure a local image workstation at the imaging center (including in one aspect a DICOM conversion interface) for interfacing with the remotely located, central management system of the ASP. Other interested healthcare providers and patients outside of the imaging clinic would also greatly benefit from having access to a remote image viewing system for viewing and storing the electronic images available from the ASP, but without requiring them or the imaging center to pay for the viewing system.

SUMMARY OF THE INVENTION

The present invention provides a medical image management system and method that reduces the high financial cost, resource allocation, time, and unreliability associated with conventional production, transportation, and viewing of conventional film-based systems and methods.

The invention in another regard also provides a medical image management system and method that reduces the need for purchasing and/or managing sophisticated technology at medical imaging centers.

The invention also provides a medical image management system that directly addresses the needs of the referring physicians and other healthcare providers located outside of the imaging center and having interest in medical image studies.

The invention also provides a medical image management system and method that integrates diagnostic and other analytical software, algorithms, or other tools associated with medical images within one, central medical image management ASP.

The present invention also provides a medical image management system and method that pushes electronic records containing medical images to healthcare providers outside of the medical imaging center soon after the medical images are taken so that the healthcare providers may view the images without the need to remotely access a central image storage cite and find and download a specific, desired image for viewing.

The invention also provides a medical image management system and method that keeps a medical image history record of times and locations where electronic records containing medical images are pushed to and viewed by parties such as healthcare providers and patients outside of the medical imaging center, and that communicates the medical image history record to the medical imaging center which produces the image.

The invention also provides a medical image management system and method that transmits lossless or substantially lossless medical image records to healthcare providers outside of the medical imaging center without requiring the healthcare provider to spend a significant amount of time to access and view the associated medical images.

Accordingly, one mode of the invention provides a medical image management system that includes a medical imaging system, a local image workstation, and a central data management system. The medical imaging system produces an electronic record in a computer-readable format and that comprises an electronic image associated with a region of a patient's body. The local image workstation communicates with the medical imaging system along a local interface such that the electronic record may be transmitted from the medical imaging device and received by, the local image workstation. The central data management system communicates with the local image workstation along a remote interface such that the electronic record may be transmitted from the local image workstation and received by the central data management system. The central data management system is also configured to push the electronic record to a pre-determined remote viewing system in a format such that the electronic record may be read and the electronic image converted to a recognizable, visible format.

According to one aspect of this mode, at least one of the medical imaging system, the local image workstation, and the central data management system is adapted to transmit the electronic record in a DICOM format. In another regard, the central data management system is adapted to receive and process the electronic record in a DICOM format.

According to a further aspect, in the event the medical imaging device does not produce the electronic record in a DICOM format, the local image workstation is adapted to convert the non-DICOM electronic record into receives into a DICOM format for transmission to the central data management system.

According to another aspect, the central data management system pushes the electronic record to the remote viewing station in a substantially uncompressed form with respect to the original size. In one more particular variation, the central data management system is adapted to push the electronic record to the remote viewing station without the electronic image being compressed more than about 3 times with respect to the original size. Further to an alternative embodiment, the central data management system pushes the electronic record to the remote viewing station with substantially lossless compression with respect to the original form and size. In another regard, the record is pushed with no loss. In still a further variation, there is at least about 1.5 times compression with respect to the original record size.

According to another aspect of this mode, the remote interface uses the internet. In another aspect, the remote interface uses a digital subscriber line (DSL) interface.

According to another aspect, the medical imaging device may be any one of the following: magnetic resonance imaging devices, CT scanner devices, ultrasound devices, computed tomography devices, nuclear medicine devices, and digital radiography or X-ray devices.

According to another aspect, each one, taken individually, or both of the central data management system and local image workstation have storage systems adapted to store the electronic record.

The system according to this mode may also further include a remote image viewing system that communicates with the central data management system along a second remote interface such that the electronic record is pushed from the central data management system and received by the remote image viewing system. The remote image viewing system may also have its own storage system which is adapted to store the electronic record. This aspect of the system may also further include an image history record system having a remote history record system associated with the remote image viewing system and a central history record system associated with the central data management system. The remote history record system sends a remote system message along the second remote interface to the central history record system and includes information related to at least one of: a time that the electronic record is received at the remote image viewing system, a time that the electronic record is opened at the remote image viewing system, and a time that the electronic image is viewed at the remote image viewing system. This image history record system may also in a further variation include a local history record system associated with the local image workstation, such that the central history record system is adapted to send a central system message along the second interface to the local history record system with at least a portion of the information contained in the remote system message.

According to still a further aspect of this mode, the central data management system comprises an internet-accessible applications service provider (ASP) with an application which is adapted to perform an operation based upon the electronic record that produces a result that is useful in managing the patient's healthcare. In one variation, this application comprises a radiology information system (RIS) that is adapted to store healthcare management-related data with the electronic image as a part of the electronic record. In a further variation, the RIS stores healthcare billing-related information in the electronic record. In another further variation, the RIS stores time-based scheduling-related information associated with the patient's healthcare in the electronic record.

Still another aspect of this mode includes a printer that is adapted to interface with at least one of the medical image system, local image workstation, or central data management system and which is adapted to print a recognizable, visible film associated with the electronic image.

Another mode of the invention provides a medical image management system with a medical imaging means, an image storage means, and an imaging pushing means. The medical imaging means is located at a first location and is for producing an electronic record in a computer-readable format and that includes an electronic image associated with a region of a patient's body. The pushing means pushes the electronic record along a remote interface to a remote image viewing system at a second location that is remote from the first location. Further to this mode, the electronic record is pushed in a format that may be opened such that the electronic image may be converted into a recognizable, visible format.

One aspect of this mode also provides a viewing means associated with the remote image viewing means for viewing the electronic image at the second location. Another aspect also provides means for providing information related to the patient in the electronic record. Yet another aspect provides a DICOM conversion means for converting the electronic record from a non-DICOM format to a DICOM format. Still a further aspect of this mode provides an image history record means for maintaining an image history record related to at least one of the transmission of the electronic record, the receipt of the electronic record, and the viewing of the electronic image. In one regard, this image history record means maintains an image history record related to each of the transmission of the electronic record, the receipt of the electronic record, and the viewing of the electronic image. In one highly beneficial variation, the image history record means includes: means for centrally managing the image history record at a central data management system located at a third location which is remote from the first and second locations; means for communicating the image history record from the central data management system to a local image workstation at the first location; and means associated with the local image workstation at the first location for displaying the image history record.

Another aspect of this mode provides DICOM conversion means for converting the electronic record from the medical imaging means into a DICOM format.

Further to another highly beneficial and desirable aspect of this mode, the image storing means includes a local storage means, a remote storage means, and a central storage means. The local storage stores the electronic record at the first location. The remote storage means stores the electronic record at the second location. The central storage means stores the electronic record at a third location that is associated with a central data management system and that is remote from the first and second locations. In one more detailed variation of this multi-storage aspect, the central storage means comprises a back-up storage means for storing the electronic record at a fourth location that is remote from the first, second, and third locations.

One further aspect of the pushing means according to this mode includes a local pushing means and a central pushing means. The local pushing means is at the first location and pushes the electronic record to a central data management system at a third location which is remote from the first and second locations. The central pushing means is associated with the central data management system at the third location and pushes the electronic record from the third location to the remote image viewing system at the second location.

Another further aspect of the pushing means according to this mode includes a central data management system at a third location that is remote from the first and second locations. The central data management system receives the electronic record from the first location and pushes the record to the remote image viewing system at the second location.

According to still a further aspect of this mode, a display means associated with the remote image viewing system displays the electronic image in a recognizable, visible format at the second location.

Another mode of the invention provides a medical image management system with a local image workstation, a central data management system, and a remote image viewing system, all respectively configured and networked such that the local image workstation pushes the electronic record via the central data management system to the remote image storage system. More specifically, the local image workstation communicates with a medical imaging system along a local interface at a first location. The local image workstation receives an electronic record that includes at least in part an electronic image from the medical imaging system associated with a body of a patient. The central data management system communicates with the local image workstation along a first remote interface from a second location that is remote from the first location, such that the central data management system receives the electronic record from the local image workstation. The remote image viewing system communicates with the central data management system along a second remote interface from a third location that is remote from the first and second locations. The remote image viewing system has a remote image storage system adapted to store the electronic record in a computer readable format, and is adapted to open the electronic record from the remote image storage system and to convert the electronic image into recognizable, visible form.

According to one aspect of this mode, the central data management system has a central image storage system that is adapted to store the electronic record in a computer-readable format. In one further variation, the central image storage system includes a back-tip storage system that is adapted to store the electronic record in a computer-readable format at a fourth location.

In another aspect of this mode, the local image workstation includes a local image storage system that stores the electronic record.

According to another aspect, the system further provides an image history record system associated with at least one of the local image workstation, central data management system, and remote image viewing system. This image history record system maintains an image history record that contains history information related to at least one of locations where the electronic record has been sent, locations where the electronic record has been received, times when the electronic record has been sent to a location, times when the electronic record has been received at a location, times when the electronic record is opened at a location, and times when the electronic image is viewed at a location.

One more variation of this image history record system according to the present mode also provides a remote history record system associated with the remote image viewing system, and a central history record system associated with the central data management system. The remote history record system sends a remote system message from the remote image viewing system to the central history record system and which contains the history information related to activity at the remote image viewing system. The central history record system sends a central system message to the local history record system and which contains at least a portion of the history information contained in the remote system message. In a further more detailed variation the local image workstation is configured to display the history information.

Another mode of the invention is a medical image management system with a medical imaging system, a local image workstation, and means for pushing the electronic image to a remote image viewing, system in a format such that the electronic record may be converted in order to represent the electronic image in a recognizable, visible format.

The medical imaging system produces the electronic record that comprises an electronic image associated with a region of a patient's body in a computer-readable format. The local image work-station communicates with the medical imaging device such that the electronic record may be transmitted from the medical imaging device and received by the local image workstation.

One aspect of the pushing means according to this mode further includes a central data management system, local pushing means for pushing the electronic record from the local image workstation to the central data management system, and remote pushing means for pushing the electronic record from the central data management system to the remote image viewing station.

According to another aspect, the system further includes means for displaying the electronic image at the remote image viewing system.

According to still a further aspect, the system also includes a means associated with the central data management system for processing, the electronic image in order to produce a result that is useful in the patient's healthcare management. This processing means in one highly beneficial variation includes Alzheimer's diagnostic analysis of the electronic image. Another highly beneficial variation includes MR spectroscopy application to the electronic image.

Another mode of the invention provides a medical image management system with a particular central data management system. The central data management system includes a computer which communicates with an electronic transmission means along a first remote interface and electronically receives an electronic record from the electronic transmission means that includes an electronic image associated with a region of a patient's body. The computer also communicates with a remote image viewing system along a second remote interface and pushes the electronic record in a DICOM format to the remote image viewing system.

According to one aspect of this mode, the system also includes a local image workstation that communicates with a medical imaging system that produces the electronic image along a local interface at a first location. The central data management system communicates with the local image workstation along a remote interface from a second location remote from the first location in order to receive the electronic record from the local image workstation. In one more detailed variation, the local image workstation transmits the electronic record, and the central data management system receives the electronic record, in the DICOM format.

According to another aspect of this mode, the central data management system is associated with an image history record system that maintains an image history record with information related to at least one of: locations where the electronic record has been sent from the central data management system, locations where the electronic record has been received from the central data management system, times when the electronic record has been transmitted from one location to another location, times when the electronic record has been received at one location from another location, times when the electronic record is opened at a location, and times when the electronic image is viewed at a location.

Another aspect of this mode includes a storage system associated with the central data management system and which stores the electronic record in at least two relatively remote locations.

Another mode of the invention is medical image management system with a local image workstation which communicates with a medical imaging system along a local interface in order to electronically receive an electronic record from the medical imaging system that includes an electronic image associated with a region of a patient's body. The local image work-station also communicates with a central data management system along a remote interface in order to push the electronic record to the central data management system. The local image workstation is also adapted to receive and display a message from the central data management system related to an image history record with history information that related to at least one of: locations where the electronic record has been sent from the central data management system, locations where the electronic record has been received from the central data management system, times when the electronic record has been transmitted from one location to another location, times when the electronic record has been received at one location from another location, times when the electronic record is opened at a location, and times when the electronic image is viewed at a location.

Another mode of the invention is a method for managing medical images. The method includes in one regard receiving along a first remote interface an electronic record, which includes an electronic image that is associated with a body of a patient, from a medical imaging system located at a first location and at a central data management system located at a second location that is remote from the first location. The method further includes pushing the electronic record from the central data management system along a second remote interface to a remote image viewing system located at a third location that is remote from the first and second locations.

One aspect of this mode further includes transmitting a central system message from the central data management system and to the local image workstation, wherein the central system message transmitted includes history information that comprises at least one of: locations where the electronic record has been sent from the central data management system, locations where the electronic record has been received from the central data management system, times when the electronic record has been transmitted from one location to another location, times when the electronic record has been received at one location from another location, times when the electronic record is opened at a location, and times when the electronic image is viewed at a location.

Another aspect of this method mode further includes receiving the electronic record at the remote image viewing system and opening the electronic image at the remote image viewing system, wherein the history information comprises the time and location of the receiving and viewing of the electronic image at the remote image viewing system. This aspect also includes communicating the history information from the remote image viewing system and to the central data management system via a remote system message before sending the central history message from the central data management system to the local image workstation.

Still another aspect of this method mode includes applying an application to the electronic image using the central data management system, wherein the application produces a result that is useful in the patient's healthcare management. The method according to this aspect further includes attaching the result to the electronic record to form a supplemented electronic record, and transmitting the supplemented electronic record from the central data management system to at least one of the local image workstation and the remote image viewing system. One particular beneficial variation of this aspect includes using an application that produces a result useful in diagnosing a parameter associated with Alzheimer's Disease. Another variation includes applying an MR spectroscopic analysis of the electronic image.

Another aspect of this mode includes pushing the electronic record from the central data management system to the remote image viewing system in a DICOM format.

Still a further aspect includes pushing the electronic record to the remote image viewing system without substantially compressing the electronic image.

Yet another aspect includes pushing the electronic record to the remote image viewing system after performing substantially loss-less compression to the electronic image.

The systems and methods of the invention for managing medical images electronically over remote interfaces such as via the internet also allow for a highly economical method for providing a medical image management ASP in a manner that expands the bottom line for medical imaging centers in particular. Therefore, the invention also includes various modes associated with the economical cost-flow related to the implementation and use of the medical image management sytems of the invention.

Another specific mode of the invention therefore is a method for providing medical image management system. The method provides a local image workstation that communicates with a medical imaging system managed by a medical imaging center along a local interface at a first location. The local image workstation is configured to receive multiple electronic records from the medical imaging system each comprising at least one electronic image that represents at least a portion of a patient's body. The method also provides a central data management system that communicates with the local image workstation along a remote interface from a second location that is remote from the first location. The method also provides a remote image viewing system that communicates with the central data management system along a second remote interface from a third location that is remote from the first and second locations. Once the local image workstation, central data management system, and remote image viewing systems are installed and interfaced, the method further includes pushing the electronic records from the local image workstation to the remote image viewing system via the central data management system and along the first and second remote interfaces.

Further to this mode, the prior recited steps are performed while charging only the medical imaging center a predetermined, fixed, periodic fee for the pushing of the electronic records through the central data management system regardless of the volume of electronic records pushed per modality. The party responsible for receiving the images at the remote image viewing system is not charged for the viewing system, which is generally downloadable, or for the receipt of the images. The imaging center is not charged for the local image workstation or for the transmission of any given image in a direct way. Regardless of how many images are sent via this system, or to how many places, the imaging center pays the same One aspect of this mode further includes providing a communication link for the first and second remote interfaces with the central data management system via an IP address associated with the central data management system on the internet.

Another aspect of this mode further includes providing the remote image viewing system at least in part by providing software that is downloadable over the second remote location onto a computer at the third location. In one particularly beneficial variation of this aspect, the software may be downloaded free of charge.

According to another aspect, the local image workstation comprises a computer, and the local image workstation including the computer is provided to the medical imaging clinic for use in the medical image management system without directly charging the medical imaging clinic for the local image workstation.

Still further to another aspect, the method also includes providing a medically useful diagnostic application on the central data management system that is adapted to perform a diagnostic operation on the electronic image at the central data management system to produce a medically useful result, and communicating the result to at least one of the local image workstation or the remote image viewing system in a computer readable form, wherein the result is provided without directly charging the medical imaging clinic or a user operating the remote image viewing system on a per-use basis of the diagnostic application.

An alternative embodiment of the invention provides a polling system located with the remote workstation, viewer or system. The polling system is an automated system within the remote workstation or viewer that polls the central data management system for queued data. The polling system may poll the central data management system on a preset schedule or periodic basis. It may also poll for data upon occurrence of a predetermined triggering event. Such events may, for example be booting the computer, a predetermined log in, establishing or re-establishing an internet connection, detecting a change in an assigned IP address.

The polling system includes: an IP address identifier, IP address notifier, a data request device and an internal poller. The IP address identifier internally determines the connection status and IP address, e.g., assigned by an internet service provider. The IP notifier, after proper authentication, notifies the central database of the current IP address. The data request device requests queued data from the central data management system. The internal poller polls the viewer, workstation or system for the occurrence of a predetermined event that triggers the IP address notification and/or data request.

In variation of this embodiment, the polling system is provided with the image push system that uses push technology as described above. According to this embodiment, the polling system will notify the central data management system of the image system, workstation or remote viewer's IP address. The central data management system will store the last known IP address in its database, for example, in a look up table. When the central data management system receives an image or other data, it will attempt to push the image or other data to the last known IP address of the specified remote location. The central data management system pushes data to locations over the Internet using push technology known to one of ordinary skill in the art, in the unique medical image delivery application and system described above with respect to FIGS. 1–6. If the delivery fails after a predetermined number of attempts, the data will be placed in a queue in the central data management system with a destination identifier that identifies the intended recipient. The central data management system delivers the queued data to the remote location when the remote module's polling system notifies the central data management system of the its current IP address or when the polling system requests delivery of queued data.

The data delivered by the central data management system may be the image itself or related information, for example, the review history, radiologist or physician notes, text, voice-overs, time, date and person reviewing the images, comments, instructions, as well as other information relating to diagnosis, treatment or the patient's medical record.

Another aspect of the invention provides an internal polling system within the local image station for communicating IP address information to the central data management system. Accordingly, in a similar manner, the local system will update its IP address information and request queued data stored in the central data management system. The central data management system will then send queued data such as information concerning delivery and review status of the delivered medical image, to the local system.

In one embodiment, the polling system within a particular module sends a signal to the central data management system when a particular event has occurred. The signal may either update the IP address and/or request queued data that was not successfully delivered to the module. The event may be, e.g., turning on the system, rebooting the system, connecting to the internet, reconnecting to the internet, internet server IP address reassignment or the expiration of a preset time interval. In this regard, the module's internal software may be structured so that when the module is turned on or booted, the execution program includes sending a signal to the internal poller that an event has occurred. Alternatively, the programming may directly instruct the notification and request device to update the IP address or request queued data from the central data management system. Additionally, the software may be structured to conduct periodic internal polling for changes such as IP address change or loss of Internet connection. For example, the IP address may be identified and stored in a file. Periodically, the stored address will be compared with the current IP address identified to the module to determine if a change has occurred. Such programming may be accomplished by way of computer programming techniques generally known in the art.

The polling event may be the passing of a predetermined time interval. For example, on a periodic basis, the polling system may check the central database for queued data and/or may update the central database's look up table containing IP addresses.

The central data management system tracks delivery attempts and maintains a database of such attempts, successes and failures. As described above, the central data management system stores the images and any associated data including delivery and access information, whether originating from a local system, remote system or the central data management system.

The polling system of the present invention provides efficient image delivery to locations or modules that do not have static IP addresses. The system is compatible with more economical, dial-up Internet services. If, for example, an Internet server is designed to switch or change IP addresses during a session, the change in IP address may be updated in the central database.

DETAILED DESCRIPTION OF THE INVENTION

The present invention provides a medical image management system (1) and method that, in one particular beneficial mode using the known "Internet" communications network, functions as an "Applications Service Provider" (ASP), which terms are herein intended to mean an information management service that is centrally accessible from various remote locations. The following are specific embodiments which are contemplated among the benefits associated with the ASP and other aspects of the invention:

1. Electronically deliver medical images in electronic record form to referring physicians, surgeons, radiologists, other healthcare providers, patients, and other interested authorized, parties outside of the imaging center, preferably via "push" technology.

2. Electronically store each image at three separate locations: locally at the imaging center and at two fully redundant, secure, central data centers (and possibly a fourth storage at the remote viewing location).

3. Provide authorized, secure and fast access to the stored image data.

4. Provide special clinical and visualization applications centrally for the benefit of remote users at remote viewing systems.

The present invention will revolutionize the process of image delivery by use of a global broadband network that will connect imaging centers and hospital radiology departments with their radiologists and referring doctors. The invention provides immediate access to patient images, allowing the same diagnostic imaging information to be available at several locations immediately after completion of the procedure. Just as the fax machine completely changed the way doctors received imaging reports, (supplanting the US Postal Service, making the process faster and much more cost efficient), the present invention is believed to represent a similar revolution in the distribution of digital medical images. With the recent advent of broadband Internet connections, which by the end of 2001 will be available to the majority of the population in the form of Digital Subscriber Lines (DSL), continued adoption of this communication mode by the healthcare community will expand the significant transition in the way images are managed between remote locations according to the management system and method of the invention.

Figure 1:
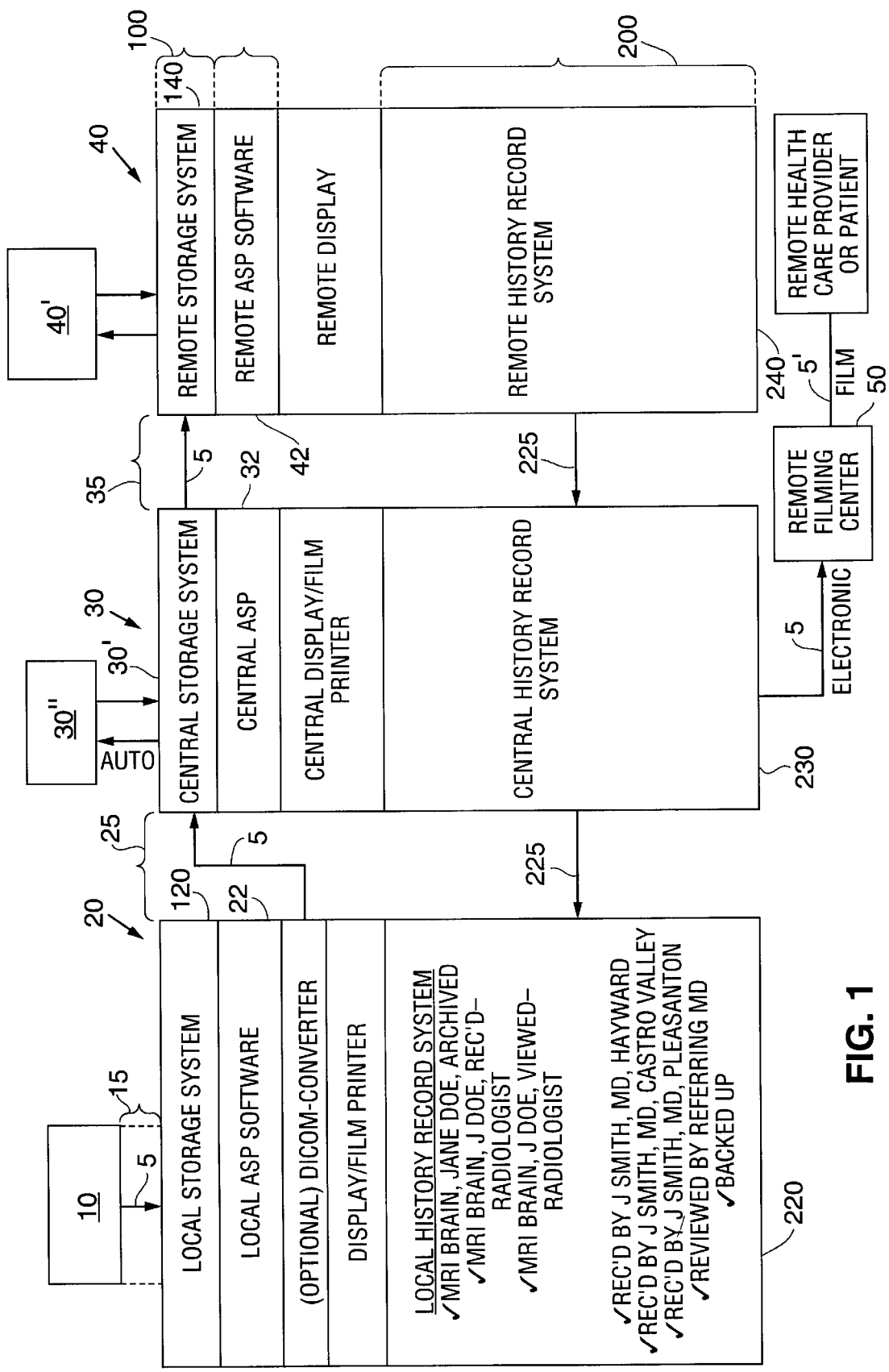
FIG. 1 shows a schematic overview of the medical image management system of the invention.

According to the invention as shown in FIG. 1, medical image management system (1) includes a medical imaging system (10), a local image workstation (20), a central data management system (30), and a remote image viewing system (40), which together provide an efficient, resource-effective, Internet-based ASP for the immediate electronic delivery and storage of medical images. In addition, an image history record system is also provided which allows for efficient tracking of when and where electronic records associated with images are transmitted, opened, and stored.

Figure 2:
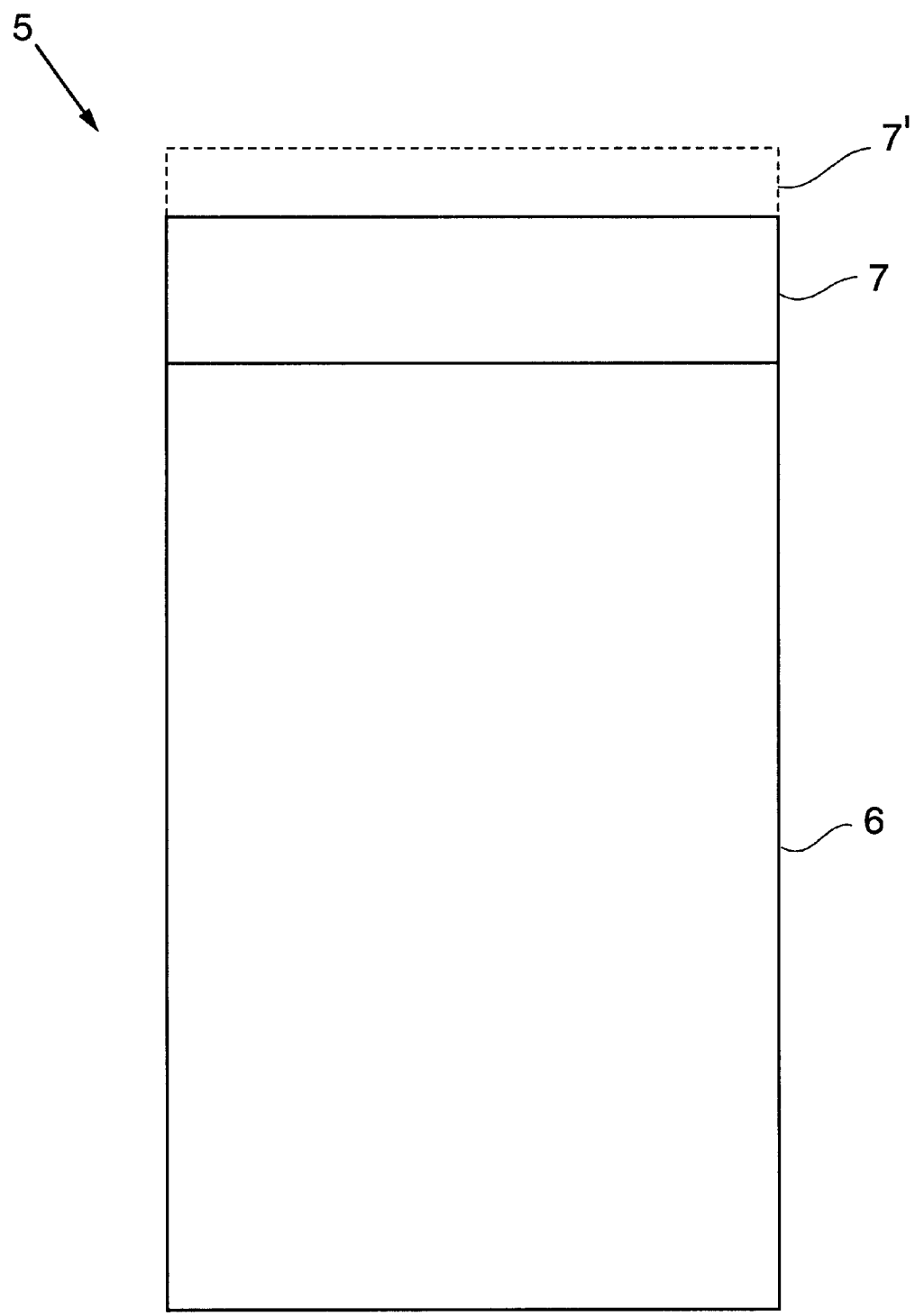
FIG. 2 shows a schematic representation of an electronic record having an electronic image and other header information associated therewith which is communicated between remote locations according to the system of FIG. 1
Figure 3:
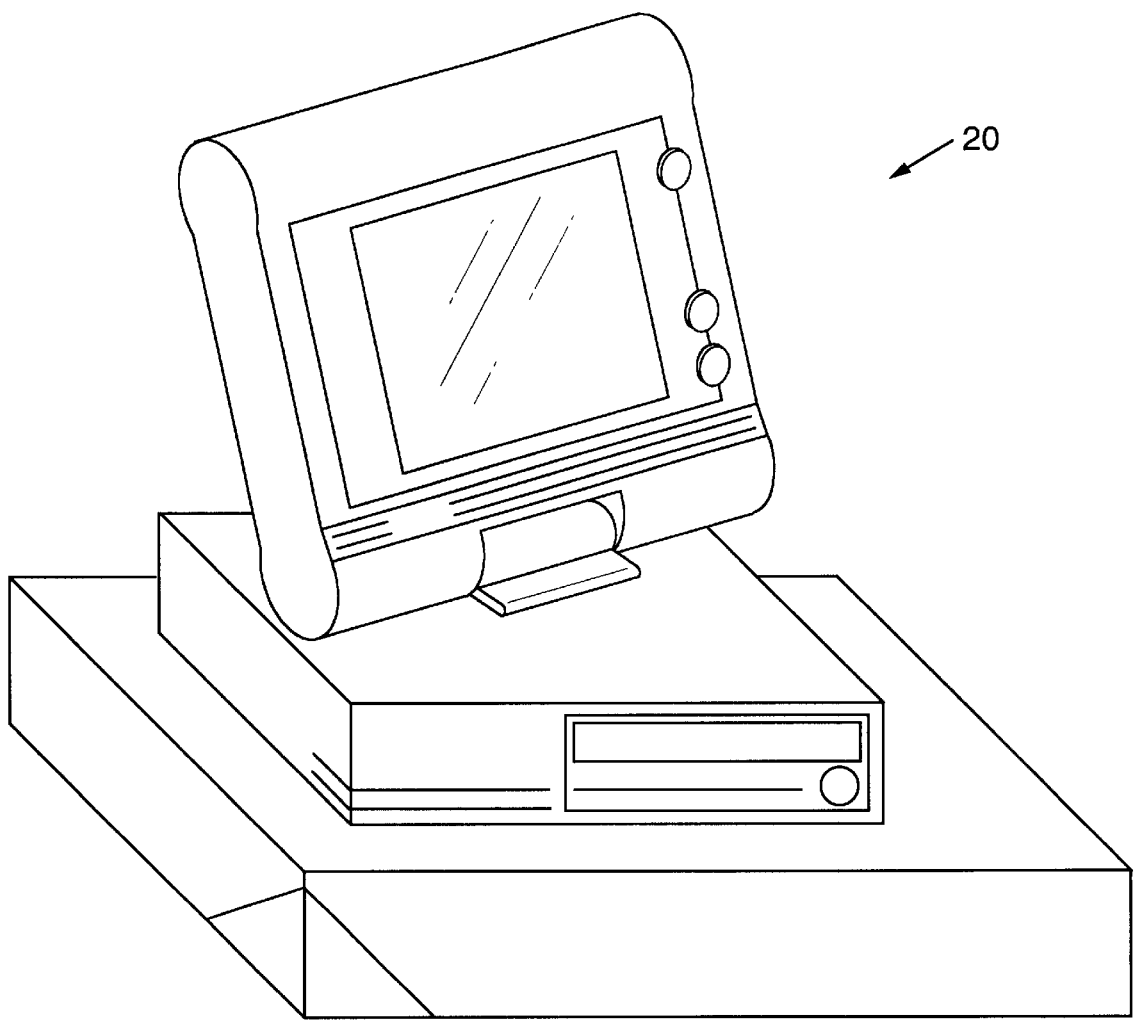
FIG. 3 shows a perspective view of hardware for the local image workstation used according to the invention.

The overall system (1) of the invention is used in one general embodiment according to the following method, which is further shown in finer detail in flow-chart format in FIGS. 5A–D. A patient study or exam is conducted at a medical imaging center using medical imaging system (10) to obtain a set of images associated with a targeted region of a patient's body. These images are provided by the medical imaging system in an electronic form as electronic images (6) that are a part of an electronic record (5), as shown in FIG. 2 and further explained in detail below. The technologist performing the exam transfers the electronic record to local image workstation (20) which is also located onsite at the imaging center. The local image workstation (20) is shown in overview in FIG. 3 for the purpose of general illustration. Local image workstation (20) archives the data locally, and then "pushes" (as explained in detail below) the electronic record to central data management system (30) at a remote location, as described in detail below.

If the imaging system (10) does not output the images packaged in the format Digital Imaging and Communications in Medicine (DICOM) compliant format, local image workstation (20) will convert the data into the DICOM format prior to transmission to central data management system (30) at a remote location with respect to the imaging, center. Once the electronic record (5) is received at central data management system (30), it is stored at that remote location and automatically routed., again via "push" delivery (described in more detail below), to one or more remote image viewing systems (40) at the respective radiologist, referring physician or surgeon, or other healthcare provider who is at another location remote from both the imaging clinic and the central data management system (30) locations. Where a radiologist is receiving electronic record (5) for viewing and interpretation/diagnosis, the radiologist in one aspect may produce a report containing new information that may be attached to the electronic record (5) and updated to the referring physician or surgeon. In addition, an image history record system (200) maintains an image history record with information regarding transmission and viewing records associated with the electronic record, and routes the respective information in the record back from these remote viewing stations, through the central data management system (30), and to the local image workstation (20) at the imaging center that produced the original image.

More detail of each component of this overall medical image management system as contemplated according to the invention is provided as follows.

Medical Imaging System

As mentioned above, the present invention broadly contemplates use of a medical imaging system (10) that provides images in electronic form for electronic delivery. In particular, the invention is believed to be highly beneficial for providing a useful ASP for managing images associated with studies conducted on MRI and CT medical image systems. In addition, the invention also contemplates the following imaging modalities as suitable substitutes for medical image system for use according to the overall medical image management systems and methods of the invention: ultrasound, computed tomography, nuclear medicine, digital radiography, etc.

Local Image Workstation

Local image workstation (20) is located at the medical imaging center and communicates with a medical imaging system (10) generally onsite at the center's location via a local interface (15). The terms "'local interface" are herein intended to mean interfaces that use locally managed and generally non-publicly accessed and used networks and routers. For the purpose of further illustration, local interfaces according to the intended meaning include without limitation hard-wired direct interfaces, extensions of data paths, and locally routed and/or managed LANs or telecommunication interfaces such as telephone lines that when used according to the invention do not extend beyond a locally and generally privately managed and used router and therefore generally do not use publicly accessed and used telecommunications networks, nodes, or routers.

In one highly beneficial embodiment, local image workstation (20) uses direct capture (as described above) to acquire the electronic image data from the imaging system. This ensures that the exact digital data, as stored on the imaging system, both in terms of matrix size and pixel depth, is transferred to the system of the invention. A physician or other healthcare provider can window and level (control brightness and contrast) as well as zoom and measure pathology with this data set. The physician can also use reference images to know the exact location of the image inside the body. These features are generally not present with frame-grabbed images, which again represents the technique employed by some other known electronic medical image management systems. The other advantage of this direct capture is that the image quality on the receiving end is as good as it is on the shipping end, which means that the image quality is the same as the MRI or CT technologists performing the study sees on the computer.

This contrasts with "secondary" capture methods like video frame-grabbing and film digitization, as described above. Most digital imaging modalities store pixel values as 14 or 16-bit values. The "direct" capture method ensures that the complete 14 or 16-bit information is transferred to the system of the invention. In the case of secondary capture some of the information is lost because the secondary capture technique generally only captures the S-bit analog representation of the image pixel data. Also secondary captured images cannot be manipulated to the same degree. As mentioned above, because of the inherent drawbacks of secondary captured data, the American College of Radiology (ACR) standard states that the direct capture method is preferred for primary diagnosis.

Further, the ACR standard recommends that the DICOM standard be used. Most currently installed medical imaging systems do not output the digital data in the standard DICOM complaint format. Therefore, according to this aspect special interfaces may be required to accomplish "direct" capture by generally converting the non-DICOM record to the DICOM format. Such interface may be provided as a separate DICOM workstation located between the local image workstation (20) and either the medical image system or the central data management system (30) that receives the output from the local image workstation (20). Or, the invention may also incorporate interfaces directly into the local image workstation (20) that enable the direct capture of data generated by many MRI systems, such as by providing a DICOM conversion technology within the architecture of local image workstation (20). One example of such a DICOM-converting interface is commercially available from Image Enhancement System, Inc. (IES), a California corporation, Another example of such an interface is commercially available by MERGE Technologies, located in Milwaukee, Wis. Interfaces to other imaging systems may also be used or otherwise developed and integrated in the overall system and methods of the invention so as to extend the reach of the invention to those imaging systems as well. Interfaces that may be developed for MRI, CT, and other radiological imaging devices are contemplated under the present invention.

It is to be further understood that the present invention contemplates all the benefits of the systems and methods herein described without the need for a local image workstation that is peripheral to the medical imaging system if that imaging system incorporates into its own architecture the necessary communication modes for interfacing and communicating with the other components of the invention as herein shown and described.

Central Data Management System

Central data management system (30) is generally located remotely from the medical imaging center, and communicates with local image workstation (20) via a remote interface (25). Central data management system (30) is also generally located remotely from the remote image viewing systems (40) to where electronic records (5) are to be sent from the central data management system (30). Therefore, central data management system communicates with these remote image viewing systems remotely, for example via remote interface (35) as shown in FIG. 1.

The term "remote" is herein intended to mean sufficient distance away from a location such that interfacing with devices at the location is generally performed in standard course using a remote interface. The terms "remote interface" are herein intended to mean interfaces that use wide area networks (WANs) or other publicly accessed and centrally managed networks or routers such as for example cable networks and publicly accessed telecommunications networks, nodes, and routers. Therefore, in another sense remote interfaces are communication interfaces that reach beyond local interfaces as described herein. In one highly beneficial mode, the remote interfacing with the central data management system (30) for the push transfer of images to and from that central image management system will employ fast digital lines and flow over the Internet. DSL, cable, ISDN and wireless modalities will also serve as suitable alternatives for remote interface connectivity.

As an internet-based ASP, the central data management system (30) will include collocation and web hosting that may be provided for example by advanced servers such as is commercially available from Exodus. Exodus has managed services using state-of-the-art tools and experience in the key areas of storage performance optimization and security. Servers such as available from StorageTek or the Exodus Network may provide a storage service for data backup and restore solutions. A further architectural aspect of the central data management system (30) may also employ for example the Exodus giga-byte Internet service which offers speed that is 10 times as fast as conventional LANS as well as the Exodus Security Service pack. Services such as provided by Exodus offers 24×7 support, monitoring, redundant Internet access with fiberoptic cable from multiple providers, which eliminates any single point of failure. Physical security, power backup, fire suppression, extensive environmental systems, and mirrored backups at a separate geographic location are all offered by Exodus and may be employed according to the present invention.

The invention contemplates use of collocation facilities, operated by leading providers of such facilities like Exodus Communications, Inc., to house all the storage and computing equipment in particular associated with the central data management system (30). These facilities provide the physical environment necessary to keep the system and service of the invention up and running 24 hours a day, 7 days a week. These facilities are custom designed with raised floors, HVAC temperature control systems with separate cooling zones, and seismically braced racks. They offer a wide range of physical security features, including state-of-the-art smoke detection and fire suppression systems, motion sensors, and 24×7 secured access, as well as video camera surveillance and security breach alarms. Further, these facilities deliver very high levels of reliability through a number of redundant subsystems, such as multiple fiber trunks from multiple sources, fully redundant power on the premises, and multiple backup generators.

It is believed that most other medical image management ASP efforts are intending to use PCs with a Microsoft database on their central servers. It is further believed that such a database will be inadequate in many circumstances, in particular when dealing with the massive storage required by imaging centers and hospitals. For this reason the present invention preferably incorporates more robust database platform, such as for example an Oracle database on a Unix platform. This will ensure a high level of reliability and scalability. The central storage system of the central data management system (30) takes into account the storage and access needs of imaging center and remote users. The rationale behind the architecture is that: most recently stored data is the most frequently accessed data and requires the most expedient retrieval; and as the data ages, the frequency of access and the need for expediency decreases.

The invention's storage system uses a hierarchical storage management (HSM) scheme to exploit the cost/benefit ratios of different storage technologies while realizing an optimum design to satisfy the above rationale. This architecture combines hard disks and tape devices, managed by intelligent software, to leverage the fast access and throughput performance benefits of disks with the cost benefits of tape media. Various aspects of the medical image storage system as provided by the present invention are presented in the following table, showing the different storage media used and the duration for which the data resides on each type of storage device along with approximate costs.

| Time | Storage Device | Access Time | Cost/Mbyte |
| --- | --- | --- | --- |
| 0–30 days | Hard disk RAID | Less than 1 second | 25 cents |
| >30 days | Online tape | 1–3 minutes | 5 cents |

When data is received at the central data management system (30), it is kept on hard disk for 30 days. It is also backed up to the Primary and Secondary archives. After 30 days, the data is moved to tape media. Products like Storagetek's (Storage Technology Corp.) Virtual Storage Manager (VSM) combines hard disk, tape and software to provide high capacity and disk-like performance. By storing older data on slower media and accumulating large quantities of data on cheaper media, the storage model of the invention offers an optimum solution.

The central data management system (30) actively "pushes" the electronic records (5) and associated images (6) to the remote image viewing systems (40) of the radiologists and referring doctors as soon as the images are available. This contrasts with the "pull" model where the images are stored on a server and a user has to login and initiate a download in order to view the images. Such pull-based methods are not believed to adequately address the needs of busy surgeons and physicians who are used to having images on films delivered to them. Therefore, at each of the locations where the images would be needed, the remote image viewing station (40) would be running and available at all times on the Internet in order to achieve immediate "push" delivery of the images as soon as they become available. Similarly, it also assures prompt delivery of a report from the remote User and back through the ASP system to other locations identified. The delivery, may also be scheduled for specific times if the remote image viewing system (40) on the receiving end is known to not be available at all times Multiple deliver attempts will also be made. The acceptance of the unique mode of constant connectivity, however, will grow considering the aggressive expansion of fast, always on Internet Connections.

Figure 4:
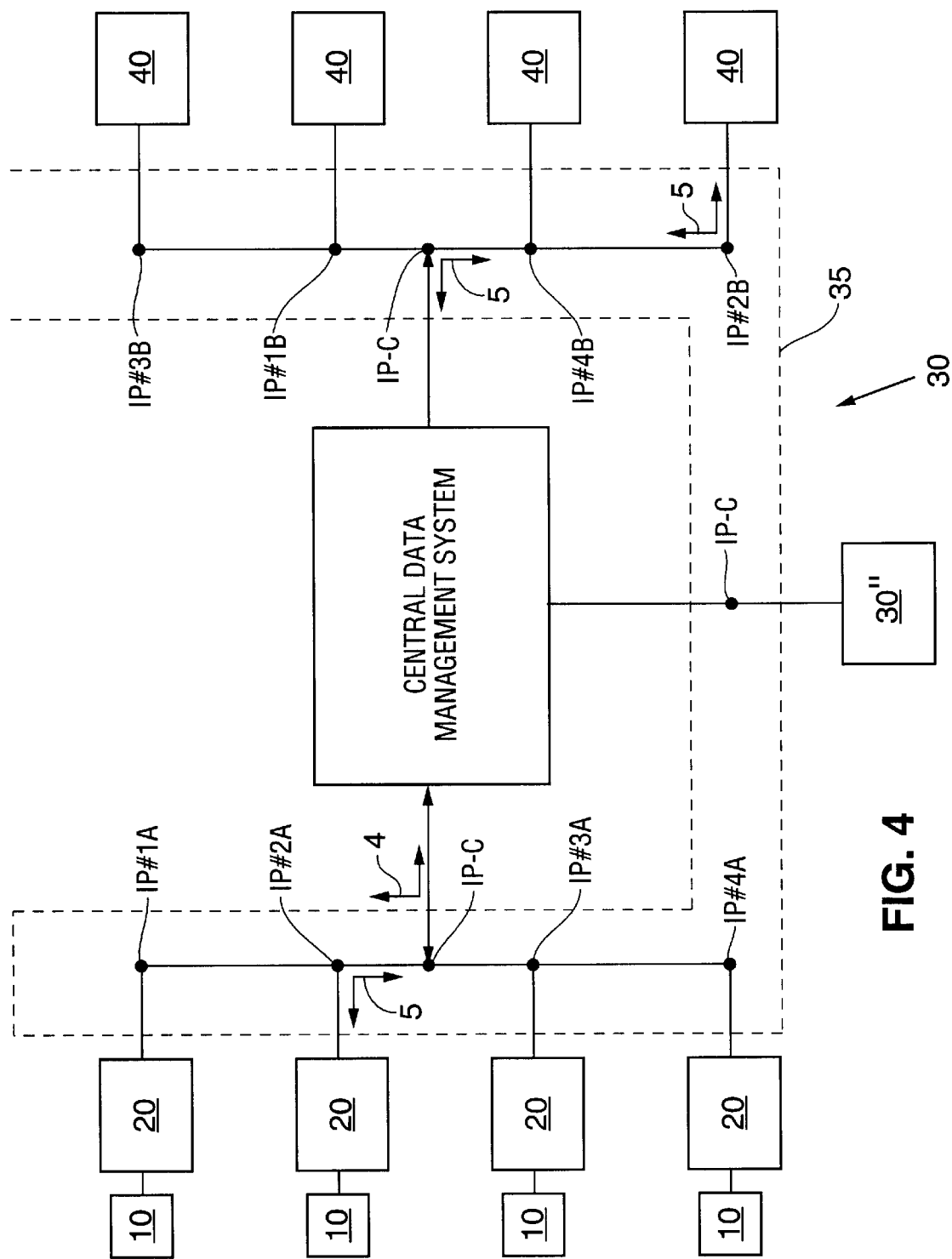
FIG. 4 shows a schematic representation of the medical image management system of the invention as it interacts via the internet with multiple medical imaging centers and multiple remote parties needed access to images.
Figure 5A:
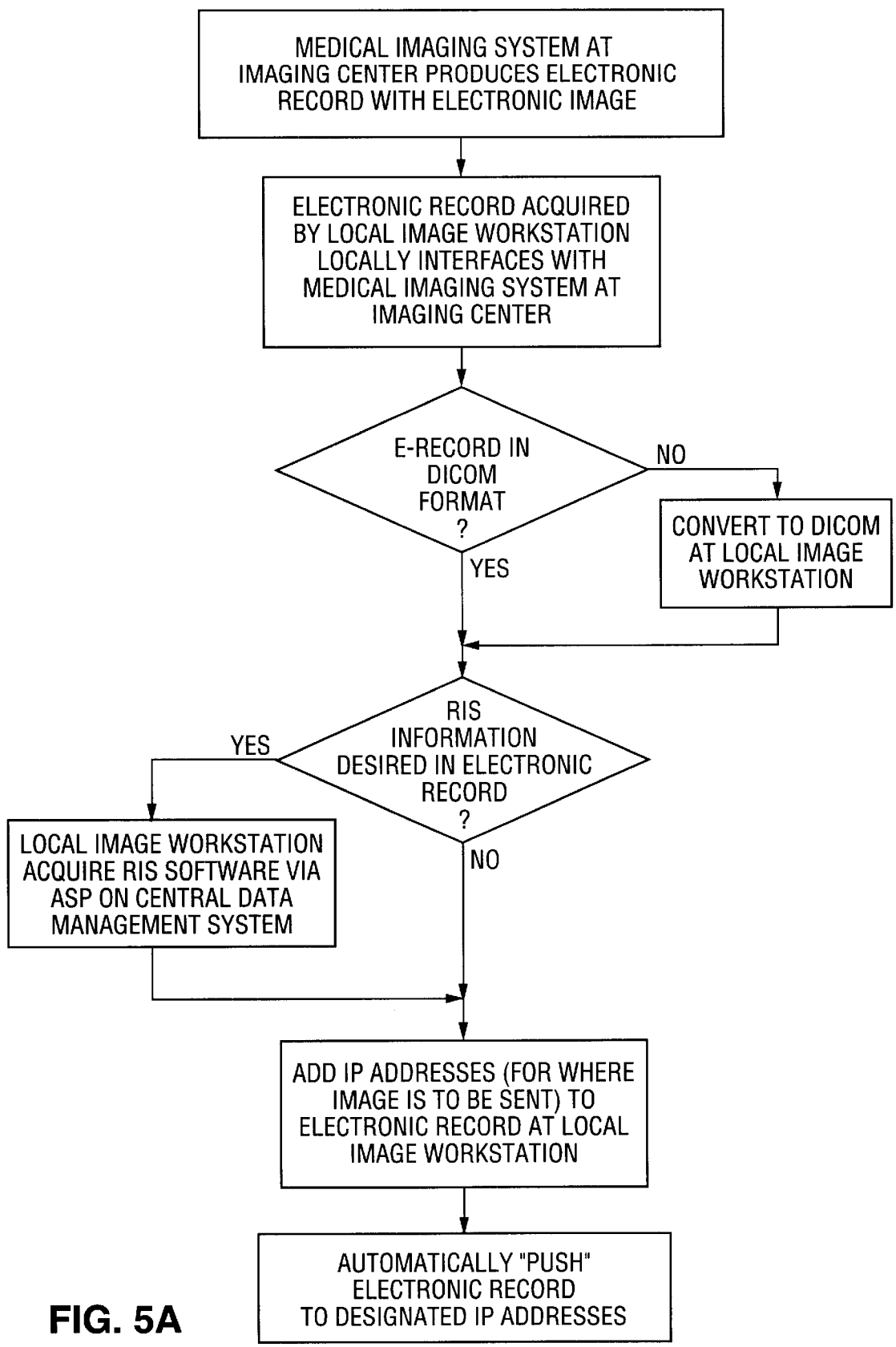
FIGS. 5A–D show various sequential modes of using the system of the invention for managing access, transport, storage, and history records associated with electronic records of medical images according to the invention.
Figure 5B:
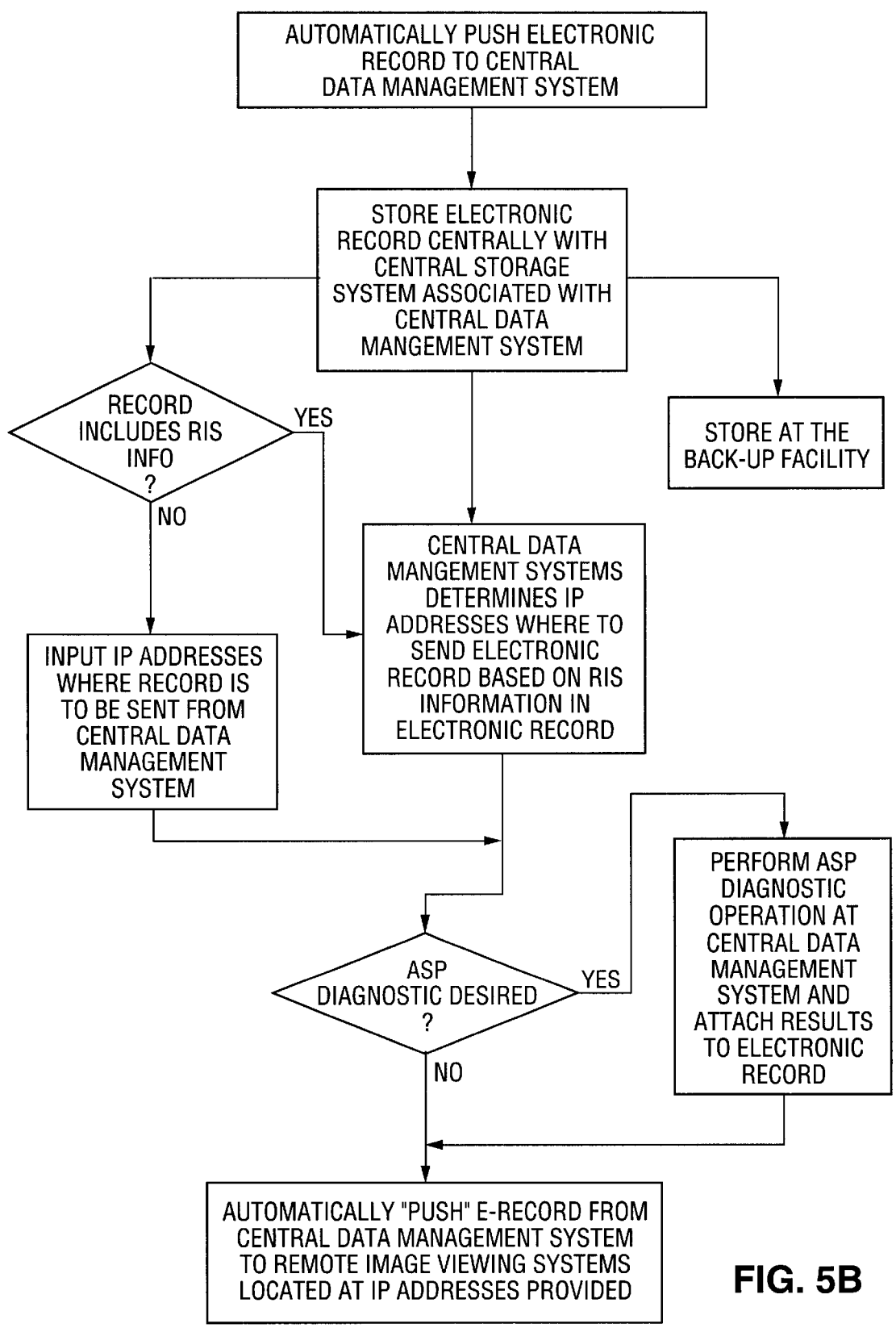
Figure 5C:
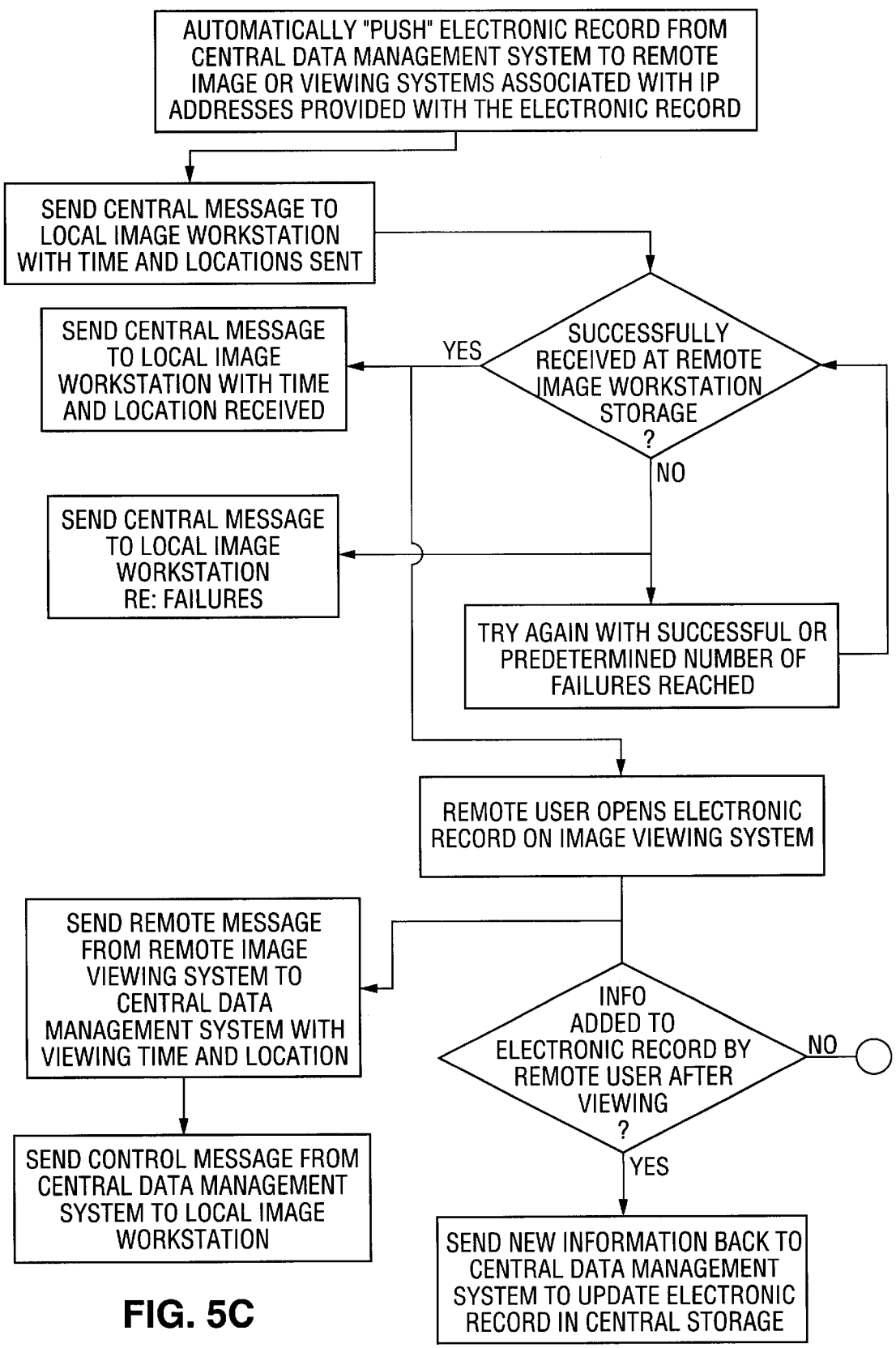
Figure 5D:
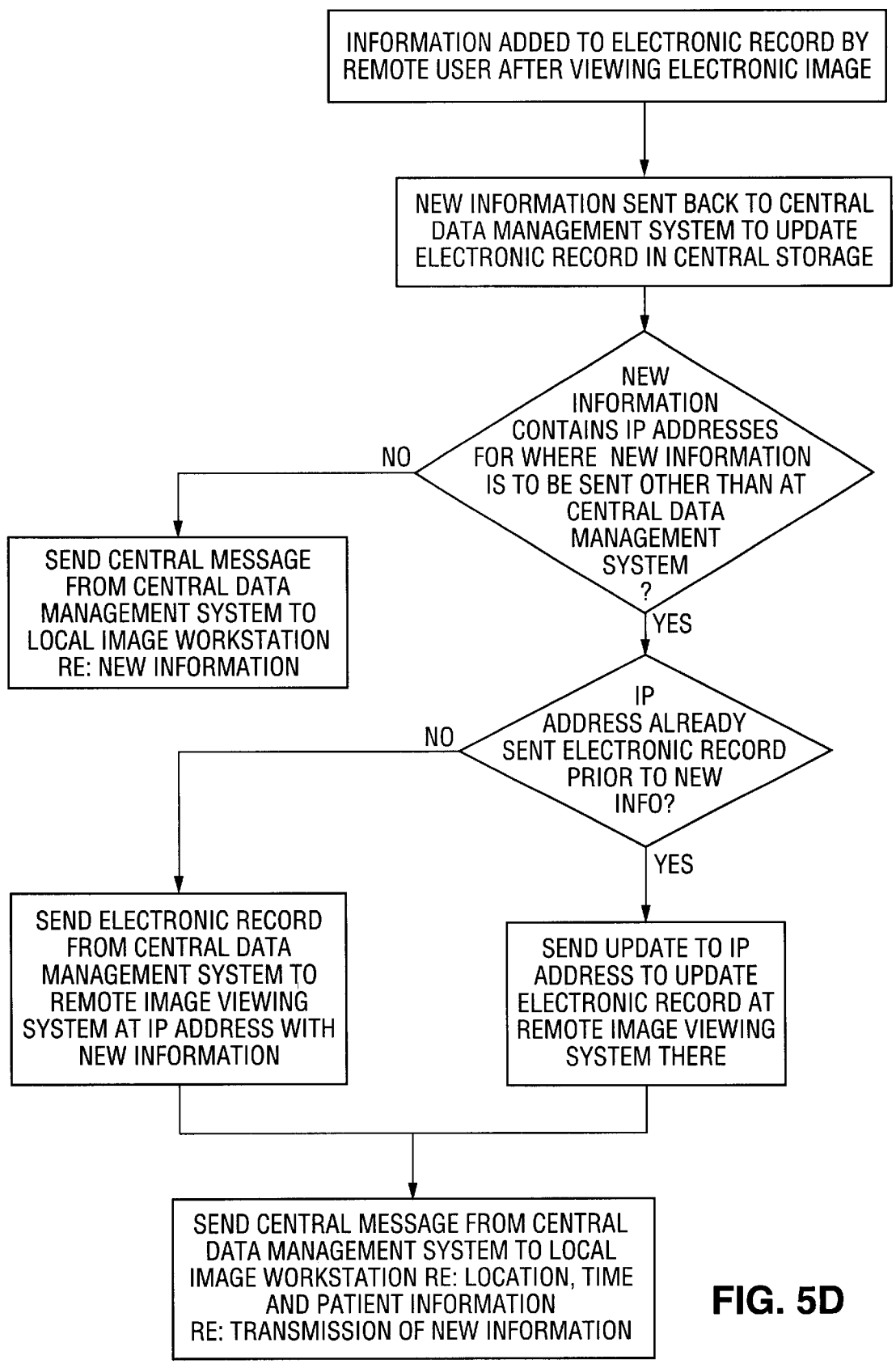
Figure 6:
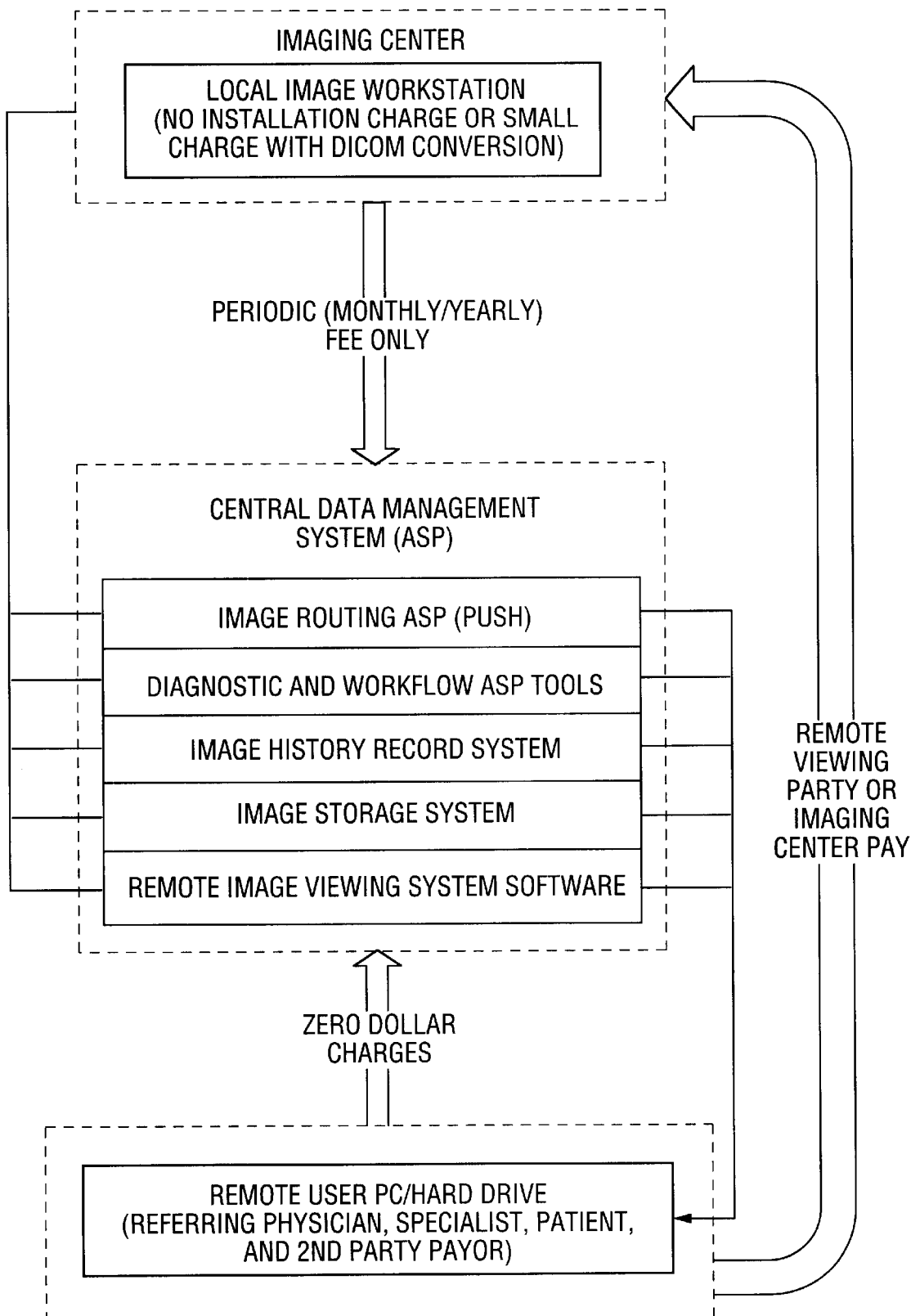
FIG. 6 shows a schematic overview of a beneficial cost-flow associated with using a medical image management ASP system according to the invention

Further aspects of using IP addresses over the Internet to assist the routing of electronic records (5) to and from various facilities via the central data management system is provided in FIG. 4. Further to this Figure, the central data management system's Internet Protocol (IP) address is generally designated as "IP-C", whereas electronic record origination addresses (local image workstations) are designated variously as IP#1A, IP#2A, etc., and destination IP addresses where the records are to be pushed are designated generally as IP#1B, IP#2B, etc. Accordingly, IP#1A pushes an electronic record (5) to central data management system (30) via its IP address IP-C, which pushes the record (5) to the desired remote image viewing systems (40) found over the internet at address IP#1B. All the desired destination addresses, including the central data management system (30) and the locations for the remote image viewing systems (40), may be designated in the header (7) associated with the electronic record (5), and may be placed there for example by manual or automated forms of entry to the record via the respective local image workstation (20).

FIG. 4 also shows electronic records (5) via flow arrows pointing in each of two opposite directions. This is intended to represent both forward and reverse flow of information related to the records (5), such as returning updated versions of the records (5) with new diagnostic information flowing from the remote image viewing system user according to various of the particular embodiments herein described and shown in the Figures. In particular, interpreting physicians, payers, and other parties outside of the medical imaging center and representing the remote image viewing systems of the invention will often attach reports to the electronic record for others to see, including the medical imaging center itself and other physicians. This is represented by the reverse flow of electronic record (5) as shown in FIG. 4, and the respective reports, etc., are shown schematically in FIG. 2 as new information (7') which is attached to the "header" or "data" section of electronic record (5) along side of the electronic image (6).

Moreover, to the extent one party with a first remote image viewing system desires to send and image to another party with a second remote image viewing system, that may be accomplished directly from the first remote image viewing system. This is shown in FIG. 1 by way of arrows between system (40) and system (40') that represents that other second remote system, which may be another physician, a patient, a third party payer, or any other authorized party. In another aspect, however, for the purpose of more centralized control, such party-to-party transfer may also require routing through the central data management system (30), and may even in some circumstances require pre-authorization via the local image workstation (20) that originally brought a given electronic record into the system.

In addition to the above mentioned "push" delivery service, a web-based "'pull" functionality will also be available to facilitate secure data access by authorized individuals from locations other than the normal delivery locations. Consistent with privacy requirements, a physician will have access to records of only those patients for whom he or she is responsible or otherwise authorized.

In contrast to other known efforts at providing a medical image management ASP, the present invention employs "push" delivery of medical images directly to the referring physician's office or offices, which may be completed according to the invention immediately after generating the image at the medical imaging center. The use of the push methodology directly addresses the needs of referring physicians prescribe the imaging study in order to diagnose or treat a patient. Clearly, these healthcare providers want the images delivered to their office(s) just as they have the films delivered today. With push delivery of electronic image records according to the invention, the image delivery will take place in the background and be on the physician's desktop computer ready for review whenever the doctor is ready to view them.

The push aspect of the invention saves costs directly equated with physician time, and is also believed to enable an increase in imaging center revenues. In one regard, referring physicians do not need to spend the time to log on to find and download the images, and in another regard medical imaging clinics that use the medical image management systems and methods of the invention will be able to use the connectivity of the overall system as a marketing advantage, attracting referring doctors and their patients who can participate in the "push" image transmission stream.

Further, the communications bandwidth requirements for speed are less stringent with the present invention's "push" model because the data transfer occurs in the background, shortly after the study is completed, and before the doctor desires to view them.

Remote Image Viewing System

In order to display and manipulate the received images, the invention in one aspect includes remote image viewing system (40) that all radiologists and referring doctors must use in conjunction with the image delivery service of the invention. The remote image viewing system in one beneficial embodiment is a software program that may be downloaded from the website associated with the central data management system (30), and run on any PC that satisfies certain minimum requirements. This program may also be available on CD ROM for distribution to doctors and/or image center users of the invention. The remote image viewing system (40) preferably gives the physician the ability to change display formats, window and level the image (adjust the brightness and contrast), magnify the image, manipulate the grayscale, measure the anatomy and pathology, easily identify spatial locations, and to the extent there is direct-capture and lossless transmission make exact measurements and determine the location of abnormalities for surgical planning.

In one further embodiment, only images delivered according to the invention will be viewable through this viewer. However, in another aspect images delivered according to the invention may be made viewable through any DICOM conformant receiver/viewer.

The remote image viewing system (40) is how physicians and other users outside of the imaging center will "experience" images transported according to the invention, and thus the system (40) Must be provided in a form that is well accepted by the medical community in particular. In a further aspect beneficial to healthcare providers, payers, and patient's alike, this viewer may be used, free of charge, to view and analyze images transported according to the invention, as further developed below.

Remote image viewing system (40) also preferably incorporates or interfaces with a database. This database in one beneficial mode is an extensive, queriable database so the physician can simply type in the patient's name or other identifying factors to bring up that particular patient immediately, even if there are hundreds of patients on the doctor's hard drive. The physicians will also be able to configure their patient image database on their computer in different ways in order to organize their patients the way they feel will be most efficient for them.

This flexibility differentiates the present invention from other medical image management ASPs that will only allow central storage of images at the company site. With the present invention, the image data, once the physician selects the patient, will be immediately downloaded into RAM on his or her computer. This allows the physician to have access quickly to the entire data set and allow for rapid change from image to image efficiently, thereby decreasing the time that the physician needs to review his patients' images. The physician will be able to view his or her patients' images even if the computer is off-line, such as when the doctor carries the laptop computer on rounds, or even to the operating room, All other known medical image management systems and methods are believed to require the physician to log on to web sites and then download the images to his computer. Hence, with other ASP systems not associated with the present invention, if the physician wishes to see his patients' images again, he must repeat the extensive and lengthy login and download procedures. It is believed that such methods which rely upon the physician to actively login and download, will be unacceptable for the referring doctors who are extremely busy and are used to images being delivered to them on film. Doctors will expect the same (image delivery to the doctor, not the doctor having, to actively seek their patient images) in the future with any digital image ASP.

The referring physicians and other users of the invention will be strongly encouraged to use DSL for interfacing the remote image viewing system (40) with the central data management system (30) of the invention since this provides for fastest and economical Internet access. Moreover, it is preferred that the Internet connection between the central data management system (30) and the remote viewing system be continuously online in order to best facilitate the "push" delivery aspect of the invention. The ability to maintain the continuous connectivity desired will improve with the ongoing, aggressive expansion of fast, always on Digital Internet Connections.

Notwithstanding the significant benefits of the electronic image flow as herein shown and described, some parties will still invariably want medical images on hard-copy film. This may also be accomplished by use of the present system as shown in FIG. 1 by sending the electronic record to a film printer (50) that converts the electronic image of electronic record (5) into film image (5') for delivery to the interested party. Because the image is stored and managed centrally, film printers that exist locally to the intended delivery location may be sent the electronic record via remote interface, and may in fact even have themselves a remote image viewing system according to the invention, at least to the extent that it is configured to open the proprietary electronic records to access the film for printing.

Diagnostic & Workflow Tracking ASP Operations

The ASP aspect of the invention also allows for specific clinical and workflow operations to be performed on the electronic image at the central image management system in a centralized and controlled environment to the benefit of all remote users of the ASP. This is shown schematically for the purpose of illustration at ASP tool (32).

In one particular embodiment, the invention provides special algorithms for processing, and analyzing images such as MRI images, such as for example in order to diagnose various conditions associated with the processed image. In one particular aspect for the purpose of further, illustration, at least one processor or software-related algorithm may be applied to the centrally stored image information in order to diagnose and stage Alzheimer's Disease. Further more detailed examples of Alzheimer-diagnostic analysis that may be offered under the ASP model of the present invention are described in the following references:

1) Meyerhoff, D. J., MacKay, S., Constans, J-M., Norman, D., VanDyke, C., Fein, G., and Weiner, M. W.: Axonal loss and membrane alterations in Alzheimer's disease suggested by in vivo proton magnetic resonance spectroscopic imaging. Annals of Neurology 36:40–47, 1994.
2) Constans, J. M., Meyerhoff, D. J., Gerson, J MacKay, S., Norman, D., Fein, G., and Weiner, M. W.: $^1$H magnetic resonance spectroscopic imaging of white matter signal hyperintensities: Alzheimer's disease and ischemic vascular dementia. Radiology 197:517–523, 1995.
3) Constans, J. M., Meyerhoff, D. J., Norman, D., Fein, G., and Weiner, M. W.: $^1$H and $^{31}$P magnetic resonance spectroscopic imaging of white matter signal hyperintensities in elderly subjects. Neuroradiology 37:615–623), 1995.
4) MacKay, S., Ezekiel, F., Di Sclafani, V., Meyerhoff, D. J., Gerson, J., Norman, D., Fein, G., and Weiner, M. W.: Alzheimer disease and subcortical ischemic vascular dementia: Evaluation by combining MR imaging segmentation and H-1 MR spectroscopic imaging. Radiology 198:537–545, 1996.
5) MacKay, S., Meyerhoff, D. J., Constans, J. M., Norman, D., Fein, G., and Weiner, M. W.: Regional grey and white matter metabolite differences in Alzheimer's disease, subcortical ischemic vascular dementia and elderly controls with $^1$H magnetic resonance spectroscopic imaging. Archives of Neurology 53:167–174, 1996.
6) Tanabe, J. L., Amend, D., Schuff, N., Di Sclafani, V., Ezekiel, F., Norman, D., Fein, G., and Weiner, M. W.: Tissue segmentation of the brain in Alzheimer's disease. American Journal of Neuroradiology 18:115–123, 1997.
7) Schuff, N., Amend, D., Ezekiel, F., Steinman, S. K., Tanabe, J., Norman, D., Jagust, W., Kramer, J. H., Mastrianni, J. A., Fein, G., and Weiner, M. W.: Changes of hippocampal n-acetyl aspartate and volume in Alzheimer's disease: A proton MR spectroscopic imaging and MRI study. Neurology 49: 1513–21, 1997.
8) Schuff, N., Amend, D., Meyerhoff, D. J., Tanabe, J., Norman, D., Fein, G., and Weiner, M. W.: Alzheimer's disease: Quantitative H-1 MR spectroscopic imaging of fronto-parietal brain. Radiology 207:91–102, 1998.
9) Schuff, N., Vermathen, P., Maudsley, A. A., and Weiner, M. W.: Proton magnetic resonance spectroscopic imaging in neurodegenerative diseases. Current Science Journal 6:800–807, 1999.
10) Tanabe, J., Ezekiel, F., Schuff, N., Reed, B., Norman, D., Jagust, W., Weiner, M. W., Chui, H., and Fein, G.: Magnetization transfer ratios of white matter hyperintensities in subjects with subcortical ischemic vascular dementia. Am J Neuroradiol 20:839–844, 1999.
11) Kwan, L. T., Reed, B. R., Eberling, J. L., Schuff, N., Tanabe, J., Norman, D., Weiner, J., and Jagust, W. J.: Effects of subcortical cerebral infarction on cortical glucose metabolism and cognitive function. Arch. Neurology 56:809–14, 1999.
12) Schuff, N., Amend, D., Knowlton, R., Tanabe, J., Norman, D., Fein, G., and Weiner, M. W.: Age-related metabolite changes and volume loss in hippocampus by proton MR spectroscopic imaging and MRI neurobiology of aging. Neurobiology of Aging 20: 279–285, 1999.
13) Capizzano, A. A., Schuff, N., Amend, D., Tanabe, J., Norman, D., Maudsley, A. A., Jagust, W., Chui, H., Fein, G., and Weiner, M. W.: Subcortical ischemic vascular dementia: Assessment with quantitive MRI and $^1$H MRSI. American Journal of Neuroradiology, (In Press 2000).

The disclosures of these references are herein incorporated in their entirety by reference thereto.

Other image processing tools such as M.R. Spectroscopy (or "Proton MRS"), may also provide an ASP tool (32) for use with the invention. Proton MRS uses the MRI scanner to listen for the radiowaves of major normal proton containing brain biochemical metabolites (myoinositol, choline, creatine, amino acids, n-acetyl aspartate) as well listening for the radiowaves of abnormal proton containing metabolites (lipid and lactate). The added metabolic bio-chemical information impacts on the differential diagnosis of abnormal lesions seen on the anatomic MRI as being either infection, tumor or stroke all of which have different treatment regiments. In certain cases proton MRS can prevent invasive neurosurgical biopsy (so called MRS brain biopsy). Proton MRS may have a future role in the early clinical evaluation process and response to therapy in dementia such as Alzheimer's Disease. Proton MRS has its own separate CPT billing code and can be performed in 5 to 20 minutes, depending on the complexity of the clinical question. Further more detailed examples of an MR Spectroscopy operation that is believed to be well suited for use under the ASP aspect of the invention is described in the following references:

1. Boyko O B, Spielman D. Clinical Applications of MR Spectroscopy. Proceedings Seventh Annual Educational Course International Society for Magnetic Resonance In Medicine, Syllabus (1999) Pages 109–119.
2. Boyko O B. Neuroimaging and Proton Spectroscopy in CNS Neoplasms. In Stark D D and Bradley W G (eds.) Magnetic Resonance Imaging, Mosby 1999.
3. Boyko O B. MR Spectroscopy of the Brain. In Tindall G (ed.) Practice of Neurosurgery, JB Saunders New York 1996.
4. Lazeyras F, Charles H C, Tupler L A, Erickson R, Boyko O B, Krishnan K R R. Metabolic Brain Mapping In Alzheimer's Disease using Proton Magnetic Resonance Spectroscopy. Psychiatry Research 82:95,1998.
5. Ross B, Michaelis T. Clinical Applications of Magnetic Resonance Spectroscopy. Magnetic Resonance Quarterly 10: 191,1994.

The disclosure of these references are herein incorporated in their entirety by reference thereto.

Such ASP-based diagnostic/image processing allows medical imaging centers using the invention to offer the respective service to a second tier of users doing business with that first doctor/user, such as for example offering the service to referring physicians, patients, and healthcare providers such as third-party payer/insurance companies. Also, the imaging center does not have to make an upfront investment in software, computer work stations and additional clinical staff—rather, the service is supplied at the central data management system (30) according to the associated ASP service. Additionally, the invention allows the owner or supplier of the diagnostic tool to reach many more patients than may be possible by creating separate, individual centers for local access and used, removing the need for example for creating a high number of localized, individual Alzheimer diagnostic centers across the country and world. The return on investment in these applications may be difficult to justify for healthcare providers such as imaging centers, radiologists, or referring physicians if such individual practice centers were required to purchase the individual applications, particularly when they are to be used in relatively rare clinical instances. Nevertheless, the applications themselves may be crucial in those specific clinical instances. Therefore, such applications when layered on top of the present invention's ASP platform will make them instantly available to a large medical community without the associated cost of ownership. As medicine becomes more complex patients will better served clinically and economically served through access to leading experts in ultra specialized procedures via the internet ASP of the present invention. Moreover, highly specialized analytical tools of the type herein disclosed can be performed with more skill, reliability and efficiency and at lower costs through the ASP aspect of the invention than under the more conventional, localized access/use modes.

The invention also contemplates ASP tool (32) as providing certain workflow software, generally referred to as "Radiology Information Systems" (RIS), for integrating the storage and communication of images with certain workflow software. RIS systems electronically attach critical patient management information (such as patient records, fee billing, and history, prior diagnosis and treatment history, etc.) to images and are generally known to provide high level, detailed workflow management capability to make radiology operations more efficient in the areas of scheduling patients, staffing, asset management, etc. The radiology community has accepted this approach, but only the largest hospitals have purchased the necessary software and hardware, due to the prohibitive cost of individual ownership. Generally speaking, known RIS technology has much higher capacity for information flow and management than individual medical imaging, centers require. Therefore, according to the RIS/ASP mode of the invention, wherever the image goes through the system of the invention, the associated patient care information also goes too—all in one integrated electronic file, and without any individual healthcare provider needing to actually purchase the RIS system. Again, by hosting this type of application as an ASP, wider and faster adaptation will result with revenue flow managed through one central site according to the various charging structures described above.

The RIS system as ASP tool (32) may be entirely managed through internet aspect to the ASP service on the central data management system (30), or it may have various components layered over the central data management system (30) in addition to the remote image viewing system (40) and/or the local image workstation (20), as shown at remote ASP interface (42) and local ASP interface (22). In particular these local and remote ASP interfaces (22, 42) may require resident architecture at the respective local image workstation (20) and remote image viewing system (40) in order to perform their role in the overall flow of information as relates to ASP-based activities on those terminal.

Image Storage System

Medical images are archived according to the invention in multiple locations according to a storage system (100) as follows.

All diagnostic studies are "medical records" and must be stored for a considerable period of time, generally for a minimum of seven years. The present invention provides a more efficient and less expensive solution for image storage, based on the Internet-based paradigm for the distribution and storage of medical images. More specifically, the invention utilizes a three-prong approach to the storage of the digital images: 1) at the remote image viewing systems (40) generally at the referring doctors' and radiologists' practice locations; 2) at two central servers associated with central data management system (30), and 3) at the local image workstations (20) located at transmitting imaging centers or hospitals. Therefore, there will be four redundant, physically separate locations where the images are stored to ensure unsurpassed reliability and efficiency in accessing image data.

The first storage location is at a local image workstation (20) at the imaging center's or hospital's own radiology department, in a DICOM format, according to a local storage system (120). This local access will make healthcare providers that use the invention feel extremely comfortable knowing that they have access to their data directly, without needing to seek permission from a third party to access their own data. A central storage system (130) associated with central data management system (30) stores all electronic records (5) at two central back-up sites (30', 30") that, are separated by considerable geographic distance. The medical imaging center and the referring doctors will have extensive access to the electronic records stored on the central backups (30'30"). A remote storing system (140) stores the electronic records (5) on the remote image viewing systems (40) at as many remote locations as the respective users wish—this allows these users, in particular referring physicians and/or radiologists, to view the images at any of a number of locations that he generally frequents in performance of his work (e.g. different office sites, hospital, etc.).

Image History Record System

The invention according to another embodiment also provides for information associated with the transport, storage, viewing, analysis, and other management of a medical image to be efficiently communicated to all interested parties, herein referred to and shown in the Figures as image history record system (200)(FIGS. 1 and 5A–D).

In one aspect, medical image centers can track the entire process of image deliver storage and review from the local image workstation (20) merely by reference to the local image workstation (20) located in their respective clinic or hospital. More specifically, a local history record system (220) displays the image history on the local image workstation (20)'s monitor, and for example notifies the clinic of each successful delivery. Also, if a delivery attempt was unsuccessful (for instance the referring doctor's computer was turned off or the Internet access was down), the customer is notified so appropriate actions can be taken to assure a quick delivery. Thus healthcare providers using the system have a degree of image management that has never been possible before with film. Furthermore, when and where the images are reviewed by the radiologist or referring physician a message may be reflected on the local image workstation (20). None of the other medical image management features with their ASP.

More specifically, remote image viewing system (40) according to one beneficial embodiment operates as follows. A remote history record system (240) associated with a remote image viewing system (40) sends a remote message (235) containing information about transmission, receipt, and viewing of the record to the central data management system (30). A central history record system (230) associated with the central data management system (30) in turn sends a central message (225) including the information from the remote message (235) to the local image workstation (20). Accordingly, all image history is updated to the imaging clinic and is accessible for review and display there, real-time, via a local history record system (220) associated with the local image workstation (20).

This image history record system (200) and associated real-time access to image transmission and use information is believed to be particularly useful when associated with the "push"-based image transmission method of the invention. Because the images are pushed to various remote locations, the message feedback methods as described is important to ensure proper management by the imaging center, and so that that practice knows what is happening to the records they have produced and subsequently distributed through the ASP of the invention.

Associated Billing, Methods

Costs associated with healthcare services such as medical imaging are highly scrutinized, and economics of imaging services are directly related to widespread availability. Beneficially, the systems and methods of the invention provide for a method of cost-flow associated with the use of the medical imaging ASP that is believed to directly address such economics in order to compel rapid adoption, in particular by free-standing medical imaging clinics that are highly sensitive in particular to up-front fees and large capital expenditures. The cost-flow method of the invention will consist of an activation fee with each clinic, that may be for example approximately $10,000 which is believed to cover all of the expenses to install the local image workstation (20) in the clinic as well as applications training expenses for both the customer and for a certain set number of referring doctors. For initial customers already having DICOM interfaces, this $10,000 fee will be waived. Since these customers already have the required hardware for electronic image transport and storage as contemplated herein, the cost to start service to these customers will be minimal. These customers will be separated geographically and the first 50–100 customers will be targeted in major cities, so that the initial users will be selected geographically from throughout the United States. This provides the widest exposure throughout the country for rapid adoption.

One cost-flow embodiment of the invention charges a fixed monthly fee, in addition to waiving installation costs in certain DICOM enabled imaging centers. This is believed to be beneficial to imaging centers or small hospitals that would have to pay $100–300 thousand up front for a PACS type system and also would need extensive IT personnel support to keep the PACS operating. The cost of using the system of the invention according to this cost-flow method is less than the cost of just the IT person who would be needed for a PACS. Moreover, PACS systems do not address the issue most important to the imaging centers: delivering the images to the referring doctors quickly and reliably. In addition, the present invention does not require the cost for secondary capture equipment and a DICOM sending station that other known medical image ASP services are believed to require. Picture Archiving and Communication Systems (PACS) generally cost $60,000 to $1,000,000, and include associated inefficiencies and costs of additional personnel to run the sophisticated hardware. According, to this invention, a monthly fee, for example of approximately $4,000 or $48,000 annually, may be charged for high performance electronic delivery, storage, retrieval, and display of the digital images. In one embodiment, this is the only fee charged, independent of volume of use. According to another embodiment, a per use fee may also be charged. In either case, the ASP-related fees represent a considerable cost savings to the clinic or hospital when compared to either use of a PACS or the current use of film. The invention therefore helps imaging centers and hospital radiology departments maximize their productivity while minimizing their costs.

Still further, the mode of charging/paying for these services is simplified under the ASP model of the invention. Rather than manufacturing and selling individual workstations or software packages to each localized physician/user, under the present invention much fewer (and possibly only one) analytical tool may be created that is thus shared by each remote user of the ASP, resulting in either a "per use" or "periodic" fee structure that does not require any one, large sum payment.

Figure 7:
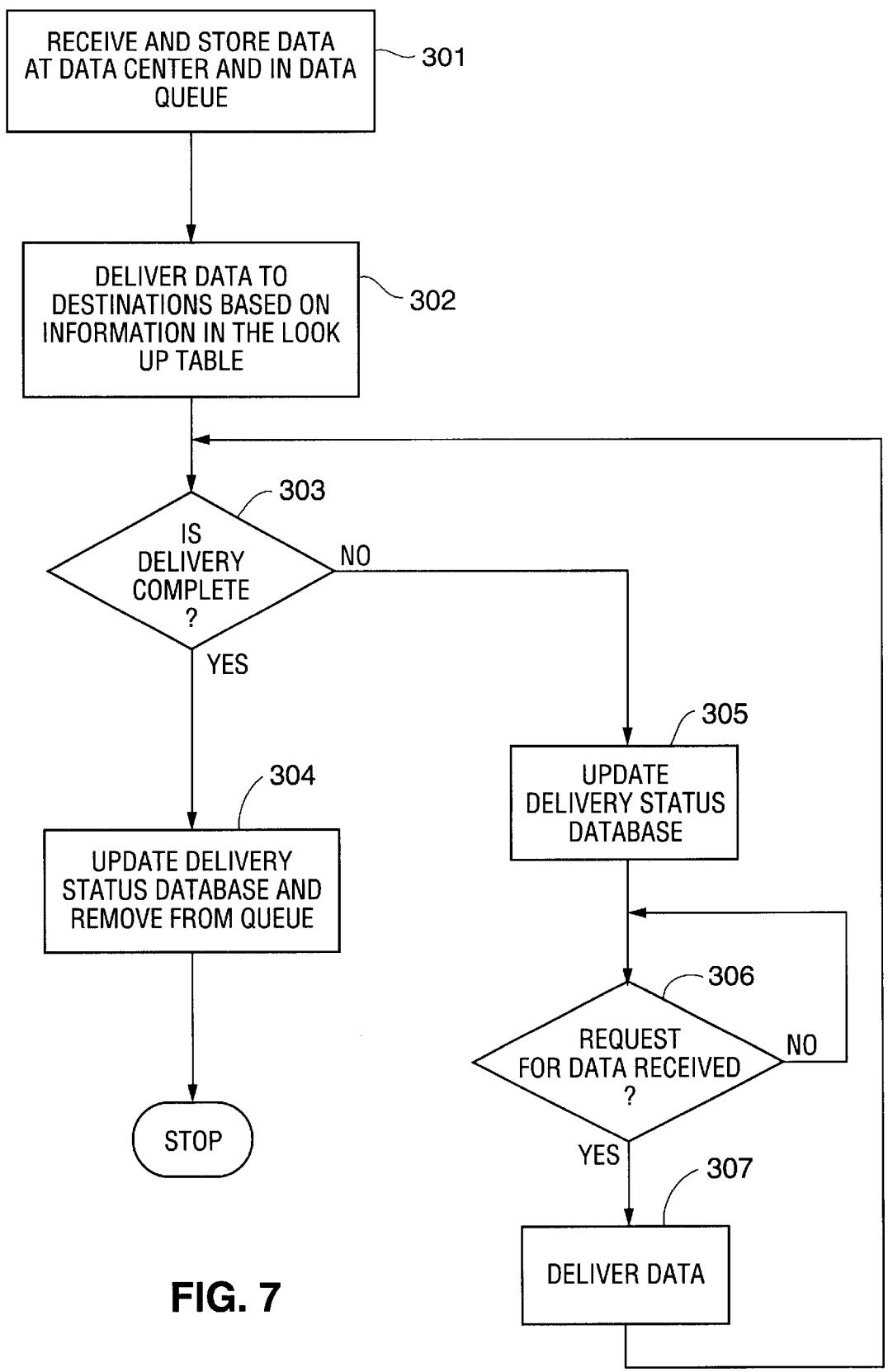
FIG. 7 shows a schematic representation of a method and system for storing, transmitting, receiving and tracking medical images and associated information of an alternative embodiment of the present invention using the polling system of FIG. 10.
Figure 8:
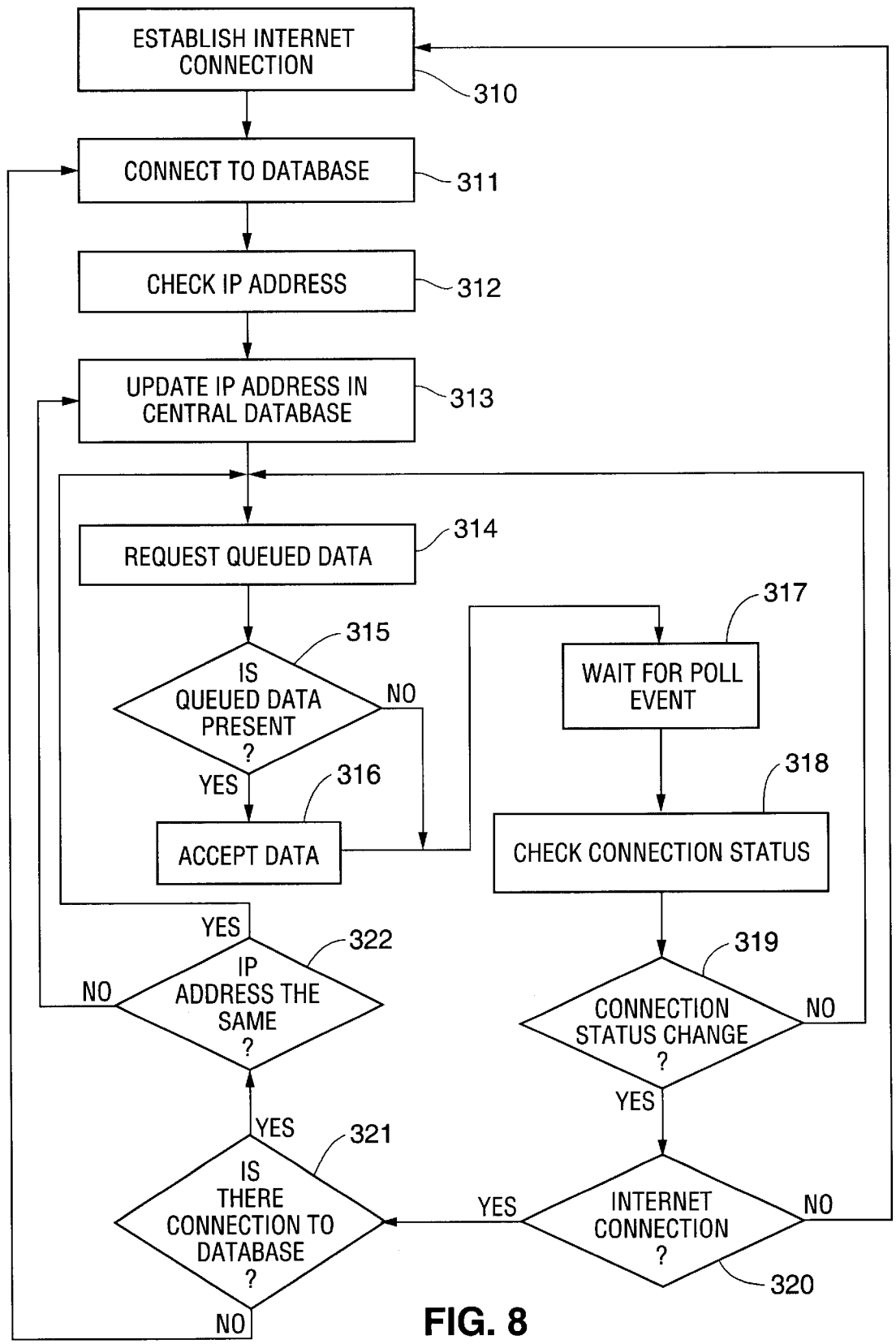
FIG. 8 shows a schematic representation of a method of using the polling system set forth in FIG. 7.
Figure 9:
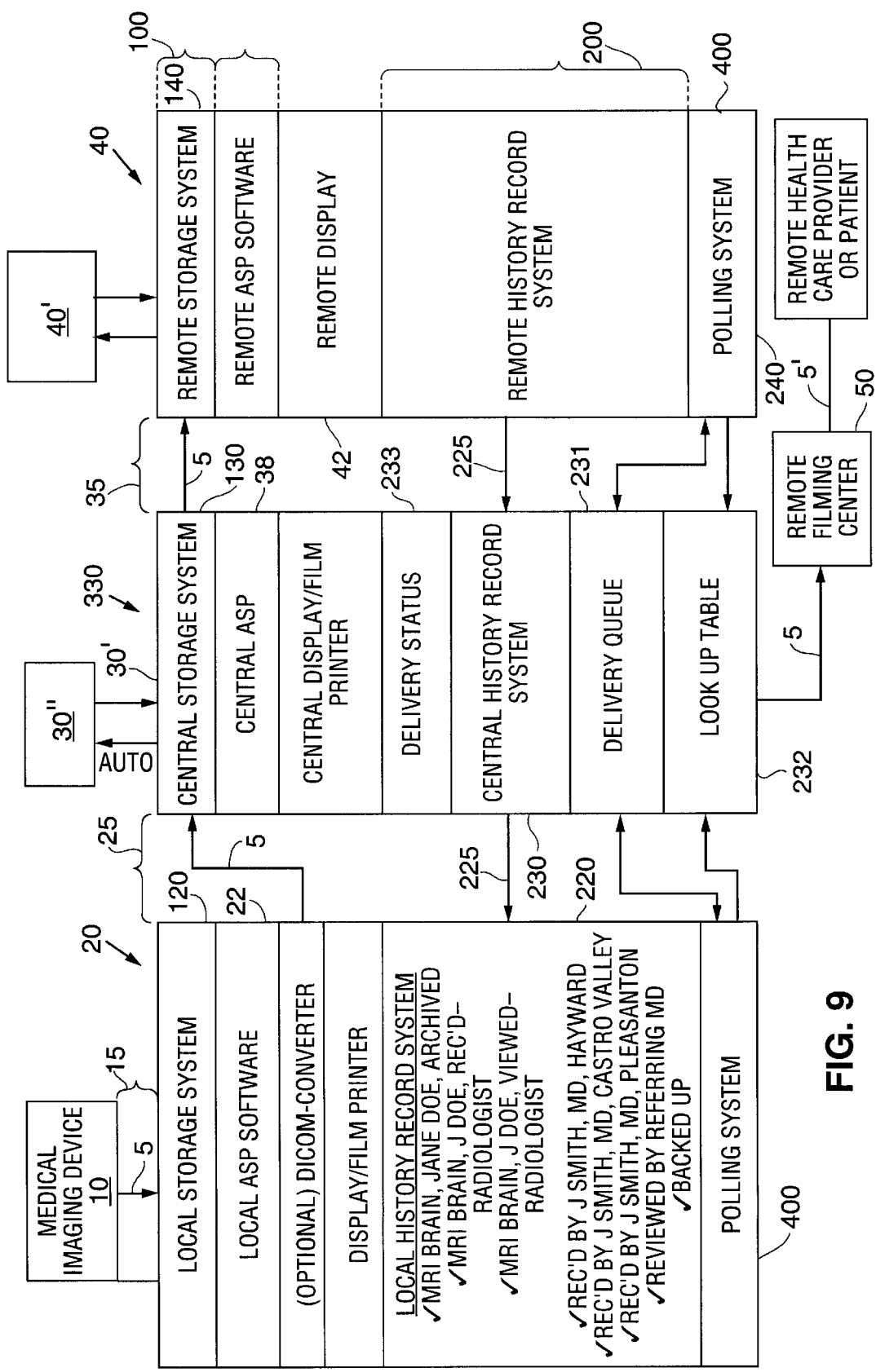
FIG. 9 shows a schematic representation of the system and method of the embodiment described with respect to FIG. 7 using a polling system illustrated in FIG. 10.
Figure 10:
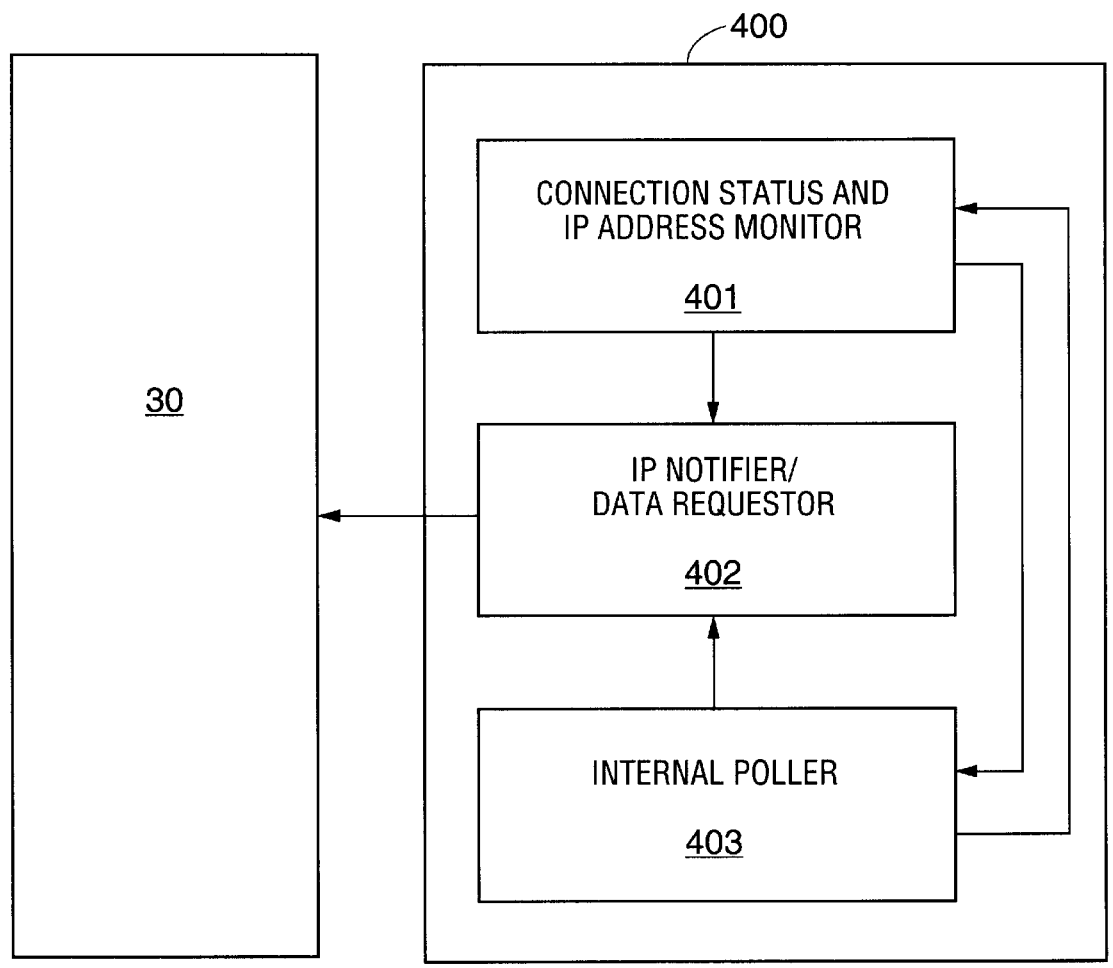
FIG. 10 shows a schematic representation of a polling system of an alternative embodiment of the present invention.

FIGS. 8 and 10 illustrate a polling system of an Alternative Embodiment. FIGS. 7 and 9 illustrate a variation of the present invention in which the medical image management system includes at least one polling system 400 as illustrated in FIG. 10. FIG. 9 illustrates a medical image management system similar to the system illustrated in FIG. 1 with like numerals representing the same elements with the corresponding description herein. The system of FIG. 9 additionally includes a polling system 400 located with each of the local image workstation 20 the remote image viewing systems 40. The polling systems 400 each communicate with the central data management system 330. The central data management system 330 further includes a delivery queue 231 that holds data for which attempted delivery has failed. Each set of data queued for delivery in the data queue 231 includes an identifier that associates the particular set of data with the intended delivery location. The identifier may also associate that data with its origin and/or its corresponding location in the central storage system 130. The central data management system 330 also comprises a look up table 232 that stores the last known IP address for each local or remote workstation, viewer or system. Finally, the central data management system 330 includes a delivery status database 233 that tracks the delivery status of all data including information relating to delivery attempts, successes and failures. In an alternative arrangement, this information may be stored with the data itself.

As illustrated in FIG. 10, the polling system 400 includes a connection status monitor 401 that tracks the Internet connection status of the module and identifies and stores the most recent IP address in an associated file. The connection status monitor 401 may also monitor the on/off status of the module, e.g., whether the module has connected to the Internet. The polling system 400 also includes an IP notifier/data requester 402 that notifies the central data management system 330 of the current IP address and/or connection status of the module. Alternatively or in addition, the IP notifier/data requestor 402 requests queued data located in the central data management system 330 as described in more detail below. The polling system 400 further comprises an internal poller 403 that checks the connection status and signals to the IP notifier/data requester 402 when an event has occurred. Such event may be, for example, booting the computer, establishing an Internet connection, a change in the IP address and/or the passing of a predetermined time interval.

Either the internal poller 403 or the connection status monitor 401 may signal to the IP notifier/data requester 402 to request queued data from the delivery queue 231 in the central data management system 330 and/or provide the look up table 232 with updated IP address information. The central data management system may be not arranged to track IP addresses or to utilizing push technology. In such a case, the IP notifier/data requestor 402 may serve simply to poll the database for data.

The internal poller 403 signals to the IP notifier/data requester 402 at the end of predetermined intervals. The internal poller 403 may also request connection status information from the connection status monitor 401 at predetermined intervals. The internal poller 403 may ask the connection status monitor 401 whether a new connection has been made. It may also ask whether the IP address has been changed. The connection status monitor 401 may also be programmed signal to the internal poller 403 when the connection status has changed. In the event that a new connection has been made or the IP address has been changed, the internal poller 403 may instruct the IP notifier/ data requestor 402 to send a signal the central data management system 330, requesting queued data and/or updating the IP address stored in the central data management system 330.

Alternatively, the connection status monitor 401 may be arranged to signal to the IP notifier/data requestor 402 when the on/off connection status or IP address of the module has changed. According to this embodiment, in the event that a new connection has been made or the IP address has been changed, the connection status monitor 401 directly instructs the IP notifier/data requestor 402 to send a signal the central data management system 330, requesting queued data and/or updating the IP address stored in the central data management system 330.

In either case, the connection status monitor 401 provides the updated IP address to the IP notifier/data requestor 402 either directly or by way of the internal poller 403.

In use, the central data management system 330, just as the central data management system 30 previously described herein, receives and stores data in the central storage system 130 and the secondary systems 30' and 30". The data may comprise, for example, an image from a local image workstation, associated patient information, review history from remote or local sites, radiologist or physician notes, text, voiceovers, comment, remote or local history records, diagnostic, treatment or other information relating to a patient's medical record. The data is also stored in the data queue 231 as illustrated in FIG. 7 (301).

The data is then pushed or delivered to the destination(s) based on information in a look-up-table 232 where the look up table 232 contains a last known IP address associated with each location 302. Push technology where information is sent to a predetermined address, is generally known in the art.

The remote module 40 then provides a confirmation as to whether or not delivery is completed 303. (The preferred embodiment is described with respect to the remote module 40, although the module at the delivery destination may be a local or remote workstation, image viewer or other interface.) If delivery is complete, the delivery status database 233 and the central history file record are updated to indicate delivery status as completed, including the time of delivery (304). The delivered data file is then removed from the queue 231.

If the delivery is not successful, then the delivery status database 233 is updated to indicate delivery failure (305). The central data management system 330 then waits until IP notifier/data requester 402 of the remote module 40 requests queued data (306) and/or updates the IP address in the look up table 232. When the request is received, that data is delivered to the IP address in the updated look up table 232 (307). This cycle is repeated until there is a successful delivery. As part of the delivery status database 233, certain files that are not delivered by a certain time may be brought to the attention of a system administrator, preferably of the data origin.

FIG. 8 illustrates the use of the polling system 400 described with respect to FIGS. 7–10 in use with the remote module or workstation 40. The remote module 40 establishes an Internet connection (310). The remote module 40 connects to the central data management system 330 (311). In this regard, the connection between the remote module 40 and the central data management system 330 may be established, for example, by way of a static or dedicated IP address, a floating IP address, or as otherwise provided by an Internet service. The remote module 40 checks its IP address by way of software within the connection status monitor 401 that monitors the connection status and determines the module's IP address (312). The steps described are not necessarily performed in this order. For example, they may be reversed.

After determining the remote module's IP address, the IP address look up table 232 of the central data management system is updated 313. This may be accomplished a number of ways. In preferred embodiments, the connection status monitor device 401 provides the updated IP address information to the IP notifier/data requestor 402 either directly or indirectly through the internal poller 403. Through internal software, the IP notifier/data requester 402 sends a signal to the look up table 232 with updated IP address information.

The local module then requests any data that may have been stored in the delivery queue 231 (for example, while the local module was offline) (314). The request is made by the IP notifier/data requestor 402 that has been instructed either by the connection status monitor 401 or the internal poller 403 to request queued data as described above.

If queued data is present (315), the data is delivered from the delivery queue 233 by way of the updated IP address stored in the look up table 232. Alternatively, if the central data management system does not have an IP address look-up table for the purpose of data deliver, the IP address from which the data request is sent, will be used to deliver the data. The data is accepted by the remote module 40 (316). Then the remote module 40 waits for an event (317). If data is not present, (315), the remote module 40 continues to wait for an event (317). The poll event may be, for example, the end of a preset interval of time, and/or another event such as booting, rebooting, connecting to Internet, reconnecting to the Internet, or detecting a reassigned IP session number.

If the push system is being used, while waiting for the poll event, any data received by the central data management system that is to be delivered to this module may be pushed to the module in a manner such as that described above.

When a poll event has occurred such as the end of a poll interval, the system checks the IP connection status (318). If the status has not changed, then the system awaits requests queued data and continues from 314. Alternatively, when the push system is used, because the connection status has not changed and the IP address located in the look-up table is the current IP address, the system instead of requesting queued data, may just continue to wait for the next polling event, i.e., return to 317 and the central data management system will send the data as it is received.

If the status has changed (319), and there is no internet connection (320), then the module is instructed to reestablish an internet connection (returning to 310). If there is an internet connection, (320) then the software instructs the connection status monitor to check to see if there is a connection with the central data management system 330 (321). If there is no connection to the central data management system then the software instructs the system to make a connection to the central data management system, returning to step 311. If there is a database connection, then the software instructs the connection status monitor 401 to determine if the IP address has changed (322). If the IP address has changed, then the a signal is sent to the central data management system 330 to update the look up table 232 with the new IP address the cycle continues at step 313. If the IP address has not changed, there is a request for queued data and the cycle continues from step 314.

The invention described above may take various forms or may be accomplished in a variety of manners. The polling system may comprise numerous software and or hardware configurations that will accomplish the described invention and are contemplated to be within the scope of the invention. The polling system may be used alone or in conjunction with a push system as described above. Other events may trigger the poll request depending on the configuration or specific needs of the viewing system (remote or local).

What is claimed is:

1. A medical image management system comprising:
    a central data management system which is adapted to receive and store an electronic record from a medical imaging device; and
    a remote image viewing system arranged to receive the electronic record and to display the record in a visible format, said central data management system and said remote image viewing system being in communication along a remote interface;
    wherein said central data management system is configured to push the electronic record to the remote image viewing system and to store the electronic record in a queue if the central data management system fails to push the electronic record; and
    wherein said remote image viewing system comprises a polling system including an internal poller to identify when an event has occurred, and a data requestor in communication with said central data management system to request queued data when said event has occurred.

2. The system of claim 1 wherein said event is a booting of the remote image viewing system.

3. The system of claim 1 wherein said event is establishing an internet connection.

4. The system of claim 1 wherein said event is a change in IP address.

5. The system of claim 1 wherein said event is the expiration of a predetermined time interval.

6. The system of claim 1, wherein the remote interface comprises a publicly accessed telecommunication interface.

7. The system of claim 1 wherein the remote interface comprises the internet.

8. The system of claim 1
    wherein said central data management system further comprises an IP address look up table including a last known IP address associated with a remote image viewing system;
    wherein said central data management system is configured to push the electronic record to the remote image viewing system at said last known IP address; and
    wherein said polling system of the remote image viewing system further comprises an IP address notifier in communication with said central data management system to notify said central data management system of the current IP address of the remote image viewing system when said event has occurred.

9. The system of claim 1 further comprising
    a second image system arranged to receive the electronic record and to display the record in a visible format, said central data management system and said second image viewing system being in communication along a remote interface;
    said second image system further arranged to receive information relating to said electronic record;
    wherein said central data management system is configured to push the electronic record to the second image system and to store the electronic record in a queue if the central data management system fails to push the electronic record; and
    wherein said second image system comprises a polling system including an internal poller to identify when an event has occurred, and a data requestor in communication with said central data management system to request queued data when said event has occurred.

10. The system of claim 9 wherein said central data management system is configured to push the information relating to the electronic record to the second image system and to store the information relating to the electronic record in a queue if the central data management system fails to push the electronic record.

11. The system of claim 10 wherein said information relating to said electronic record comprises at least one of, a review history, radiologist notes, physician notes, text, voice-overs, time, date and person reviewing images, comments, instructions, information relating to diagnosis, information relating to treatment of a patient, and information relating to a patient's medical record.

12. The system of claim 10, wherein said second image system comprises a local image workstation,
   wherein said system further comprises an image history record system associated with at least one of the central data management system and local image workstation, and which is adapted to maintain an image history record that comprises said information relating to the electronic record which comprises at least one of: locations where the electronic record has been sent, locations where the electronic record has been received, times where the electronic record has been sent to a location, times when the electronic record has been received at location, times where the electronic record is opened at a location, and times where the electronic image is viewed at a location.

13. The system of claim 12 further comprising an image history record system associated with the remote image viewing system; and
   a central history record system associated with the central data management system,
   wherein the remote history record system is adapted to send a remote system message from the remote image viewing system to the central history record system, which remote system message contains the history information related to activity at the remote image viewing system, and wherein the central history record system is adapted to push a central system message to the local history record system, which central system message contains at least a portion of the history information contained in the remote system message.

14. A medical image management system comprising:
   a central data management system which is adapted to receive and store an electronic record from a medical imaging device; and
   a remote image viewing system arranged to receive the electronic record and to display the record in a visible format, said central data management system and said remote image viewing system communicating along a remote interface;
   wherein said central data management system comprises an IP address look up table including a last known IP address associated with a remote image viewing system and wherein said central data management system is configured to push the electronic record to the remote image viewing system at said last known IP address and
   wherein said remote image viewing system comprises a polling system including a internal poller to identify when an event has occurred and an IP address notifier in communication with said central data management system to notify said central data management system of the current IP address of the remote image viewing system when said event has occurred.

15. The medical image management system of claim 14 wherein said event is the booting of the remote image viewing system.

16. The medical image management system of claim 14 wherein said event is establishing an internet connection.

17. The medical image management system of claim 14 wherein said event is a change in IP address.

18. The system of claim 14 wherein said event is the expiration of a predetermined time interval.

19. The system of claim 14, wherein the remote interface comprises a publicly accessed telecommunication interface.

20. The system of claim 14 wherein the remote interface comprises the internet.

21. The system of claim 20 wherein said information relating to said electronic record comprises at least one of, a review history, radiologist notes, physician notes, text, voice-overs, time, date and person reviewing images, comments, instructions, information relating to diagnosis, information relating to treatment of a patient, and information relating to a patient's medical record.

22. The system of claim 20 wherein said second image system comprises a local image workstation, and wherein said system further comprising an image history record system associated with at least one of the central data management system and local image workstation, and which is adapted to maintain an image history record that comprises said information relating to the electronic record which comprises at least one of: locations where the electronic record has been sent, locations where the electronic record has been received, times where the electronic record has been sent to a location, times when the electronic record has been received at location, times where the electronic record is opened at a location, and times where the electronic image is viewed at a location.

23. The system of claim 20 further comprising an image history record system associated with the remote image viewing system; and
   a central history record system associated with the central data management system,
   wherein the remote history record system is adapted to push a remote system message from the remote image viewing system to the central history record system, which remote system message contains the history information related to activity at the remote image viewing system, and wherein the central history record system is adapted to push a central system message to the local history record system, which central system message contains at least a portion of the history information contained in the remote system message.

24. The system of claim 14 further comprising
   a second image system arranged to receive the electronic record and to display the record in a visible format, said central data management system and said second image viewing system being in communication along a remote interface;
   said second image system further arranged to receive information relating to said electronic record;
   wherein said central data management system is configured to push the electronic record to the second image system and to store the electronic record in a queue if the central data management system fails to push the electronic record; and
   wherein said second image system comprises a polling system including an internal poller to identify when an event has occurred, and a data requestor in communication with said central data management system to request queued data when said event has occurred;
   wherein said central data management system comprises an IP address look up table including a last known IP address associated with the second image system and wherein said central data management system is configured to push the information relating to the electronic record to the second image system at said last known IP address associated with the second image system, and
   wherein said the second image system polling system further comprises an IP address notification device in communication with said central data management system to notify said central data management system of the current IP address of the second image system when said event has occurred.

25. The system of claim 24 wherein said central data management system is configured to push the information relating to the electronic record to the second image system and to store the information relating to the electronic record in a queue if the central data management system fails to push the electronic record.

26. A medical image management system comprising:
a medical imaging means at a first location for producing an electronic record in a computer-readable format and that includes an electronic image associated with a region of a patient's body;
a storage means for storing the electronic record;
a pushing means for pushing the electronic record along a remote interface to a remote image viewing system at a second location that is remote from the first location, wherein the electronic record is pushed in a format that may be opened such that the electronic image may be converted into a recognizable, visible format;
a queue means for temporarily storing an electronic record when it has not been successfully pushed to the remote image viewing system; and
a polling means at said remote image viewing system for requesting an electronic record stored in said queue means when a predetermined event has occurred.

27. A medical image management system comprising:
a medical imaging means at a first location for producing an electronic record in a computer-readable format and that includes an electronic image associated with a region of a patient's body;
a storage means for storing the electronic record;
a pushing means for pushing the electronic record along a remote interface to a remote image viewing system at a second location that is remote from the first location, wherein the electronic record is pushed in a format that may be opened such that the electronic image may be converted into a recognizable, visible format;
an IP address look up means for storing a most recent know IP address corresponding to a remote image viewing system;
a polling means at said remote image viewing system for updating the IP address look up means when a predetermined event has occurred.

28. A method for managing medical images, comprising:
receiving along a first remote interface at a central data management system, an electronic record from a medical imaging system located at a first location, wherein the central data management system is located at a second location that is remote from the first location, and wherein the electronic record includes an electronic image that is associated with a body of a patient; and
pushing the electronic record along a second remote interface to a remote image viewing system located at a third location that is remote from the first and second locations;
storing an electronic record in a temporary location when the electronic record has not been successfully pushed;
requesting the temporarily stored electronic record by the remote image viewing system upon the occurrence of a predetermined event.

29. The method of claim 28 further comprising
adding information to the electronic record at the remote image viewing system to create a revised electronic record;
pushing the revised electronic record to a local image workstation located at said first location;
storing the revised electronic record in a temporary location when the revised electronic record has not been successfully pushed to said local image workstation;
requesting the temporarily stored electronic record by the local image workstation system upon the occurrence of a predetermined event.

30. The method of claim 28 wherein said information added to the electronic record comprises at least one of, a review history, radiologist notes, physician notes, text, voice-overs, time, date and person reviewing images, comments, instructions, information relating to diagnosis, information relating to treatment of a patient, and information relating to a patient's medical record.

31. A method for managing medical images, comprising:
storing the IP address of a remote location in a look up table in a central data management system at a second location;
receiving along a first remote interface at the central data management system, an electronic record from a medical imaging system located at a first location, wherein the central data management system is located at the second location that is remote from the first location, and wherein the electronic record includes an electronic image that is associated with a body of a patient; and
pushing the electronic record from the central data management system along a second remote interface to a remote image viewing system located at the remote location that is remote from the first and second locations;
checking the IP address at the remote image viewing system upon the occurrence of a predetermined event and if the IP address has changed, communicating the changed IP address to the central data management system; and
updating the look up table with the changed IP address.

32. The method of claim 31 further comprising adding information to the electronic record at the remote image viewing system to create a revised electronic record;
pushing the revised electronic record to a local image workstation at the first location;
checking the IP address at the local image workstation system upon the occurrence of a predetermined event and if the IP address has changed, communicating the changed IP address to the central data management system; and
updating the look up table with the changed IP address.

33. The method of claim 32 wherein said information added to the electronic record comprises at least one of, a review history, radiologist notes, physician notes, text, voice-overs, time, date and person reviewing images, comments, instructions, information relating to diagnosis, information relating to treatment of a patient, and information relating to a patient's medical record.

34. A medical image management system comprising:
a central data system which is adapted to receive and store an electronic record from a medical imaging device;
a remote image viewing system arranged to receive the electronic record; and
a remote interface between said central data system and said remote image viewing system, wherein said central data system and said remote image viewing system are in communication along said interface,
said remote image viewing system including a polling system comprising an internal poller to identify when an event has occurred and a data requestor in communication with said central data management system to request queued data when said event has occurred.

* * * * *